US011370789B2

(12) United States Patent
Hunt et al.

(10) Patent No.: US 11,370,789 B2
(45) Date of Patent: Jun. 28, 2022

(54) OCTAHYDRO FUSED AZADECALIN GLUCOCORTICOID RECEPTOR MODULATORS

(71) Applicant: Corcept Therapeutics, Inc., Menlo Park, CA (US)

(72) Inventors: Hazel Hunt, Storrington (GB); Iain Walters, Nottingham (GB); Benoit Gourdet, Nottingham (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 45 days.

(21) Appl. No.: 16/984,914

(22) Filed: Aug. 4, 2020

(65) Prior Publication Data

US 2020/0361935 A1 Nov. 19, 2020

Related U.S. Application Data

(60) Division of application No. 16/382,474, filed on Apr. 12, 2019, now Pat. No. 10,787,449, which is a division of application No. 16/161,642, filed on Oct. 16, 2018, now Pat. No. 10,323,034, which is a continuation of application No. 16/036,001, filed on Jul. 16, 2018, now abandoned, which is a continuation of application No. 14/549,885, filed on Nov. 21, 2014, now Pat. No. 10,047,082.

(60) Provisional application No. 61/985,035, filed on Apr. 28, 2014, provisional application No. 61/908,333, filed on Nov. 25, 2013.

(51) Int. Cl.
| | |
|---|---|
| *C07D 471/04* | (2006.01) |
| *C07D 498/04* | (2006.01) |
| *C07D 519/00* | (2006.01) |
| *C07D 471/02* | (2006.01) |
| *A61P 35/00* | (2006.01) |
| *A61P 3/04* | (2006.01) |
| *A61P 3/10* | (2006.01) |
| *A61P 11/06* | (2006.01) |
| *A61P 19/02* | (2006.01) |
| *A61P 25/00* | (2006.01) |
| *A61P 31/12* | (2006.01) |
| *A61P 37/02* | (2006.01) |
| *A61K 31/4745* | (2006.01) |
| *A61K 31/5383* | (2006.01) |
| *A61K 31/4162* | (2006.01) |
| *A61K 31/437* | (2006.01) |
| *A61K 31/4738* | (2006.01) |

(52) U.S. Cl.
CPC ............ *C07D 471/04* (2013.01); *A61P 35/00* (2018.01); *C07D 498/04* (2013.01); *C07D 519/00* (2013.01)

(58) Field of Classification Search
CPC ................ C07D 471/04; C07D 498/04; C07D 519/00; A61P 35/00; A61P 3/04; A61P 3/10; A61P 11/06; A61P 19/02; A61P 25/00; A61P 31/12; A61P 37/02; A61K 31/4745; A61K 31/5383; A61K 31/4162; A61K 31/437; A61K 31/4738
See application file for complete search history.

(56) References Cited

U.S. PATENT DOCUMENTS

| | | | |
|---|---|---|---|
| 6,680,310 B2 | 1/2004 | Belanoff et al. | |
| 7,678,813 B2 | 3/2010 | Clark et al. | |
| 7,790,745 B2 | 9/2010 | Yang et al. | |
| 7,928,237 B2 | 4/2011 | Clark et al. | |
| 8,324,203 B2 | 12/2012 | Clark et al. | |
| 8,461,172 B2 | 6/2013 | Clark et al. | |
| 8,557,839 B2 | 10/2013 | Clark et al. | |
| 8,598,154 B2 | 12/2013 | Clark et al. | |
| 8,859,774 B2 | 10/2014 | Hunt et al. | |
| 8,889,867 B2 | 11/2014 | Clark et al. | |
| 9,273,047 B2 | 3/2016 | Hunt et al. | |
| 9,707,223 B2 | 7/2017 | Hunt et al. | |
| 9,943,505 B2 | 4/2018 | Hunt et al. | |
| 9,956,216 B2 | 5/2018 | Hunt et al. | |
| 10,047,082 B2 * | 8/2018 | Hunt .................... | C07D 519/00 |
| 10,117,852 B2 | 11/2018 | Hunt et al. | |
| 10,213,414 B2 | 2/2019 | Hunt et al. | |
| 10,323,034 B2 | 6/2019 | Hunt et al. | |
| 2006/0223852 A1 | 10/2006 | Gillespie et al. | |
| 2007/0281928 A1 | 12/2007 | Clark et al. | |
| 2008/0070950 A1 | 3/2008 | Benjamin et al. | |
| 2010/0292477 A1 | 11/2010 | Clark et al. | |
| 2012/0220565 A1 | 8/2012 | Clark et al. | |
| 2013/0225633 A1 | 8/2013 | Hunt et al. | |
| 2014/0315866 A1 | 10/2014 | Pan et al. | |

(Continued)

FOREIGN PATENT DOCUMENTS

| | | | |
|---|---|---|---|
| EP | 145121 | A2 | 6/1985 |
| EP | 375210 | A1 | 6/1990 |
| EP | 375210 | B1 | 5/1995 |

(Continued)

OTHER PUBLICATIONS

"Amorphous Materials: How Some Solids Flow Like Liquids", Science Daily, CNRS, Available online At: http://www.sciencedaily.com/releases/2008/07/080704153507.htm, access date Jan. 16, 2014, pp. 1-3.
"Amorphous Solid", Wikepedia, Available Online At: http://en.wikipedia.org/wiki/Amorphous_solid, Jan. 16, 2014, 3 pages.
"Database Crossfile Beilstein", Beilstein Institut Zur Foerderung der Chemischen Wissenschaft, Accession No. 101172-52-5 (BRN), Jun. 27, 1988, 3 pages.

(Continued)

*Primary Examiner* — John M Mauro
(74) *Attorney, Agent, or Firm* — Kilpatrick Townsend & Stockton LLP

(57) ABSTRACT

The present invention provides octahydro fused azadecalin compounds and methods of using the compounds as glucocorticoid receptor modulators.

15 Claims, 3 Drawing Sheets

(56) References Cited

U.S. PATENT DOCUMENTS

2015/0148341 A1  5/2015  Hunt et al.

FOREIGN PATENT DOCUMENTS

| | | | |
|---|---|---|---|
| EP | 3074011 | B1 | 7/2019 |
| JP | 322220 | B | 4/1957 |
| JP | 04368384 | A | 12/1992 |
| JP | 09505030 | A | 5/1997 |
| JP | 2002506032 | A | 2/2002 |
| JP | 2002544271 | A | 12/2002 |
| WO | 9410150 | A1 | 5/1994 |
| WO | 9504734 | A1 | 2/1995 |
| WO | 9945925 | A1 | 9/1999 |
| WO | 0069846 | A1 | 11/2000 |
| WO | 03015692 | A2 | 2/2003 |
| WO | 03061651 | A1 | 7/2003 |
| WO | 2004065351 | A1 | 8/2004 |
| WO | 2005087769 | A1 | 9/2005 |
| WO | 2009058944 | A2 | 5/2009 |
| WO | 2012027702 | A1 | 3/2012 |
| WO | 2012094618 | A1 | 7/2012 |
| WO | 2013177559 | A2 | 11/2013 |
| WO | 2010132445 | A1 | 11/2020 |

OTHER PUBLICATIONS

"Highlights of Prescribing Information", KORLYM® (Mifepristone), Corcept Therapeutics Incorporated, 2017, 7 pages.

U.S. Appl. No. 12/777,340 , "Declaration Under 37 CFR 1.132", Solid Forms and Process for Preparing, dated Feb. 2013, 5 pages.

U.S. Appl. No. 14/549,885 , "First Hunt Declaration", dated Jan. 18, 2017, pp. 1-4.

U.S. Appl. No. 14/549,885 , "Second Hunt Declaration", dated Jul. 7, 2017, 14 pages.

Barth et al., "Structural and Stereoelectronic Requirements for the Inhibition of Mammalian 2,3-Oxidosqualene Cyclase by Substituted Isoquinoline Derivatives", Journal of Medicinal Chemistry, vol. 39, No. 12, American Chemical Society, Jun. 7, 1996, pp. 2302-2312.

Christoffers et al., "Absolute Configuration of Methyl (+)-1,2,3,4,6,7,8,8a-Octahydro-6-isoquinolone-8a-carboxylate and Stereochemistry of a Copper-Catalyzed Asymmetric Michael Reaction", Zeitschrift Fuer Naturforschung B Chemical Sciences, vol. 59, No. 4, Apr. 1, 2004, pp. 375-379.

Christoffers et al., "Copper-Catalyzed Asymmetric Michael Reactions with α-Amino Acid Amides: Synthesis of an Optically Active Piperidine Derivative", Wiley Online Library, vol. 2002, No. 9, May 2002, pp. 1505-1508.

Christoffers et al., "Synthesis of an Optically Active Decahydro-6-Isoquinolone Scaffold with a Quaternary Stereocenter", Wiley Online Library, vol. 2004, No. 12, Jun. 2004, pp. 2701-2706.

Christoffers , "Transformation of an Optically Active Decahydro-6-isoquinolone Scaffold: Perfect Felkin-Anh Diastereoselectivity", Organic Letters, vol. 6, No. 7, American Chemical Society, Feb. 3, 2004, pp. 1171-1173.

Chu , "Connecting via Winsock to SIN at PTO-STN on Port 23", STN-12691012, STN International, Mar. 19, 2012, 62 pages.

Chu et al., "Successful Long-Term Treatment of Refractory Cushing's Disease with High-Dose Mifepristone (RU 486)", The Journal of Clinical Endocrinology & Metabolism, vol. 86, No. 8, Aug. 1, 2001, pp. 3568-3573.

Clark et al., "1H-Pyrazolo[3,4-g]Hexahydro-Isoquinolines as Selective Glucocorticoid Receptor Antagonists with High Functional Activity", Bioorganic & Medicinal Chemistry Letters, vol. 18, No. 4, Feb. 15, 2008, pp. 1312-1317.

Dibas et al., "Glucocorticoid Therapy and Ocular Hypertension", European Journal of Pharmacology, vol. 787, Sep. 15, 2016, pp. 57-71.

Elmore , "Nonsteroidal Selective Glucocorticoid Modulatores: The Effect of C-5 Alkyl Substitution on the Transcriptional Activation/Repression Profile of 2,5-Dihydro-10-Methoxy-2,2,4-Trimethyl-1H-[1]Benzopyrano[3,4-f]Quinolines", American Chemical Society, Journal of Medicinal Chemistry, vol. 44, No. 25, Dec. 1, 2001, pp. 4481-4491.

EP14863514.7 , "Extended European Search Report", dated May 4, 2017, 6 pages.

EP19177963.6 , "Extended European Search Report", dated Jul. 25, 2019, 5 pages.

Gasparini et al., "Peripheral Markers In Testing Pathophysiological Hypotheses and Diagnosis Alzheimer's Disease", FASEB Journal, vol. 12, 1998, pp. 17-34.

Gauthier et al., "Alzheimer's Disease: Current Knowledge, Management and Research", Canadian Medical Association Journal, vol. 157, No. 8, Oct. 15, 1997, pp. 1047-1052.

Genck , "Make the Most of Antisolvent Crystallization; A Number of Factors can Affect Solids' Formation", Available Online At: https://www.chemicalprocessing.com/articles/2010/210/, Nov. 8, 2010, 8 pages.

Greicius et al., "Presenile Dementia Syndrome: An Update on Taxonomy and Diagnosis", Journal of Neurol, Neurosurg, Psychiatry, vol. 72, 2002, pp. 691-700.

Gupta et al., "Studies on Carboxylation in Heterocyclic Systems", Journal of Scientific and Industrial Research, vol. 20B, Aug. 1961, pp. 394-397.

Hsin et al., "Stereoselective Synthesis of Morphine Fragments Trans- and Cisoctahydro-1H-Benzo[4,5]Furo[3,2-e]Isoquinolines", Elsevier Lmitited, Tetrahedron, vol. 61, No. 2, Jan. 10, 2005, pp. 513-520.

Hunt et al., "Identification of the Clinical Candidate (R)-(1-( 4-Fluorophenyl)-6-((1-methyl-1 H-pyrazol-4-yl)sulfonyl)-4 ,4a, S ,6, 7, 8-h exahydro-1 H-pyrazolo[3 ,4-g]isoqu in olin-4a-yl) ( 4-(triflu oromethyl)pyridin-2-yl)methan one (CORT12S134): A Selective Glucocorticoid Receptor", Journal of Medicinal Chemistry, vol. 60, No. 8, Apr. 3, 2017, pp. 3405-3421.

IN201617021323 , "First Examination Report", dated Feb. 20, 2020, 6 pages.

Johnson et al., "Relationships Between Drug Activity in NCI Preclinical in Vitro and in Vivo Models and Early Clinical Trials", British Journal of Cancer, vol. 84, No. 10, May 18, 2001, pp. 1424-1431.

Kugita , "Studies on the Syntheses of Hydrogenated Quinolines and Isoquinolines as Analgesics", Pharmaceutical Bulletin, vol. 4, No. 1, Feb. 1956, pp. 29-34.

Magee et al., "Construction of Cis- and Trans-Decahydroisoquinolines via Heterogeneous Catalytic Hydrogenation", The Journal of Organic Chemistry, American Chemical Society, vol. 64, No. 7, Mar. 16, 1999, pp. 2549-2554.

Mahmood et al., "3D-QSAR Comfa, Comsia Studies on Pyrazolo-Fused Azadecalins Derivatives as Selective Glucocorticoid Receptor Antagonists", Pharma Science Monitor, vol. 3, Issue 3, Jul. 2012, pp. 2027-2055.

Nakawatase et al., "Alzheimer's Disease And Related Dementia", Cecil's Textbook of Medicine, Twenty-First Edition, vol. 1. W. B. Saunders Company, 2000, pp. 2042-2045.

PCT/US2005/008049 , "International Search Report and Written Opinion", dated Jun. 15, 2005, 8 pages.

PCT/US2010/034382 , "International Search Report and Written Opinion", dated Jul. 9, 2010, 7 pages.

PCT/US2011/049408 , "International Search Report and Written Opinion", dated Jan. 30, 2012, 10 pages.

PCT/US2013/027720 , "International Search Report and Written Opinion", dated Jun. 17, 2013, 8 pages.

PCT/US2014/066759 , "International Preliminary Report on Patentability", dated Jun. 9, 2016, 6 pages.

PCT/US2014/066759 , "International Search Report and Written Opinion", dated Feb. 6, 2015, 9 pages.

Rehn et al., "Antiinflammatory Action of Glucocorticoids—New Mechanisms for Old Drugs", The New England Journal of Medicine, vol. 353, No. 16, Oct. 20, 2005, pp. 1711-1723.

Sausville et al., "Contributions of Human Tumor Xenografts to Anticancer Drug Development", Cancer Research, vol. 66, No. 7, Apr. 2006, pp. 3351-3354.

(56) References Cited

OTHER PUBLICATIONS

Schultz et al., "Heteroatom Directed Photoarylation. Synthetic Potential of the Heteroatom Oxygen", Journal of the American Chemical Society, vol. 100, No. 7, Mar. 29, 1978, pp. 2150-2162.
Schultz et al., "Studies Directed at a Synthesis of the Morphine Alkaloids. A Photochemical Approach", J. Org. Chem., American Chemical Society, vol. 50, No. 2, Jan. 1985, pp. 217-231.
Spitz et al., "Mifepristone (RU 486)—A Modulator of Progestin and Glucocorticoid Action", The New England Journal of Medicine, Massachusetts Medical Society, vol. 329, No. 6, Aug. 5, 1993, pp. 404-412.
Uchida et al., "An Efficient Access to the Optically Active Manzamine Tetracyclic Ring System", Tetrahedron Letters, vol. 40, Issue 1, Jan. 1, 1999, pp. 113-116.

* cited by examiner

OCTAHYDRO FUSED AZADECALIN GLUCOCORTICOID RECEPTOR MODULATORS

CROSS-REFERENCES TO RELATED APPLICATIONS

This application is a U.S. Divisional Application of Ser. No. 16/382,474, filed Apr. 12, 2019, which is a U.S. Divisional Application of Ser. No. 16/161,642, filed Oct. 16, 2018 (now U.S. Pat. No. 10,323,034, issued Jun. 18, 2019), which is a Continuation of U.S. application Ser. No. 16/036,001, filed Jul. 16, 2018, which is a Continuation of U.S. application Ser. No. 14/549,885, filed Nov. 21, 2014 (now U.S. Pat. No. 10,047,082, issued Aug. 14, 2018), which claims priority to U.S. Provisional Application Nos. 61/985,035, filed Apr. 28, 2014, and 61/908,333, filed Nov. 25, 2013, all of which disclosures are incorporated herein in their entireties for all purposes.

BACKGROUND OF THE INVENTION

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind the natural ligand, and is constitutively localized in the nucleus. The GR is also known as the GR-II receptor.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129). What is needed in the art are new compositions and methods for modulating GR receptors. Surprisingly, the present invention meets these and other needs.

BRIEF SUMMARY OF THE INVENTION

The present invention provides many fused azadecalin compounds. In some embodiments, the present invention provides compounds having the formula:

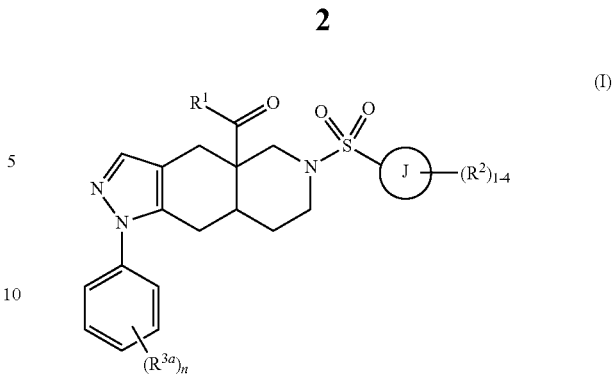

wherein $R^1$ of formula I is a heteroaryl ring having from 5 to 6 ring members and from 1 to 4 heteroatoms, which can each independently be N, O, or S, optionally substituted with 1-4 groups, which can each independently be $R^{1a}$. Each $R^{1a}$ of formula I can independently be hydrogen, $C_{1-6}$ alkyl, halogen, $C_{1-6}$ haloalkyl, $C_{1-6}$ alkoxy, $C_{1-6}$ haloalkoxy, N-oxide, or $C_{3-8}$ cycloalkyl. Ring J of formula I can be an aryl ring or a heteroaryl ring having from 5 to 6 ring members and from 1 to 4 heteroatoms, which can each independently be N, O, or S. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{2a}$R$^{2b}$, —C(O)R$^{2a}$, —C(O)OR$^{2a}$, —C(O)NR$^{2a}$R$^{2b}$, —SR$^{2a}$, —S(O)R$^{2a}$, —S(O)$_2$R$^{2a}$, $C_{3-8}$ cycloalkyl, or $C_{3-8}$ heterocycloalkyl having from 1 to 3 heteroatoms wherein each can independently be N, O, or S. Alternatively, two $R^2$ groups on adjacent ring atoms are combined to form a heterocycloalkyl ring having from 5 to 6 ring members and from 1 to 3 heteroatoms, which can each independently be N, O, or S, wherein the heterocycloalkyl ring is optionally substituted with from 1 to 3 $R^{2c}$ groups. $R^{2a}$, $R^{2b}$ and $R^{2c}$ of formula I can each independently be hydrogen or $C_{1-6}$ alkyl. Each $R^{3a}$ of formula I can independently be a halogen. Subscript n of formula I can be an integer from 0 to 3. The compounds of formula I can also be the salts and isomers thereof.

In some embodiments, the present invention provides a pharmaceutical composition including a compound of the present invention and a pharmaceutically acceptable excipient.

In some embodiments, the present invention provides a method of modulating a glucocorticoid receptor including contacting a glucocorticoid receptor with a compound of the present invention, thereby modulating the glucocorticoid receptor.

DETAILED DESCRIPTION OF THE INVENTION

I. General

Figure 1:
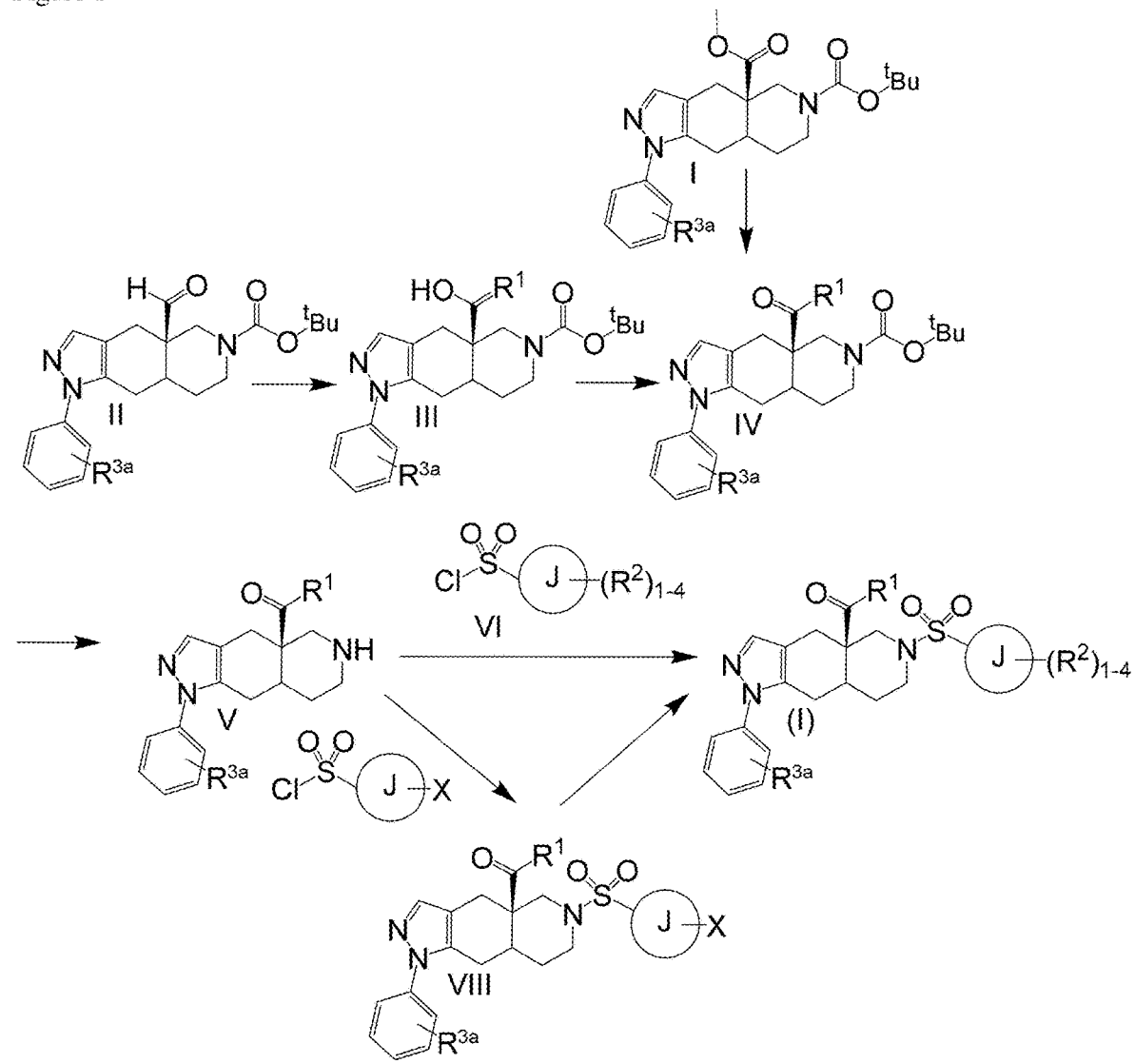
FIGS. 1, 2, 3 and 4 show various synthetic schemes for making the compounds of the present invention.

The present invention provides compounds capable of modulating a glucocorticoid receptor (GR) and thereby providing beneficial therapeutic effects. The compounds include octahydro fused azadecalins. The present invention also provides methods of treating diseases and disorders by modulating a GR receptor with the compounds of the present invention.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, N-oxide, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S or N.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Modulating a glucocorticoid receptor" refers to methods for adjusting the response of a glucocorticoid receptor towards glucocorticoids, glucocorticoid antagonists, agonists, and partial agonists. The methods include contacting a glucocorticoid receptor with an effective amount of either an antagonist, an agonist, or a partial agonist and detecting a change in GR activity.

"GR modulator" refers to compounds that agonize and/or antagonize the glucocorticoid receptor and are defined as compounds of Formula I below.

"Glucocorticoid receptor" ("GR") refers to a family of intracellular receptors which specifically bind to cortisol and/or cortisol analogs (e.g. dexamethasone). The glucocorticoid receptor is also referred to as the cortisol receptor. The term includes isoforms of GR, recombinant GR and mutated GR.

"Glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug to preferentially bind to the GR rather than other nuclear receptors, such as mineralocorticoid receptor (MR) or progesterone receptor (PR).

"Contacting" refers to the process of bringing into contact at least two distinct species such that they can react with one another or interact such that one has an effect on the other.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject in need thereof" refers to a living organism suffering from or prone to a condition that can be treated by administration of a pharmaceutical composition as provided herein. Non-limiting examples include humans, other mammals and other non-mammalian animals.

"Disorder" or "condition" refer to a state of being or health status of a patient or subject capable of being treated with the glucocorticoid receptor modulators of the present invention. Examples of disorders or conditions include, but are not limited to, obesity, hypertension, depression, anxiety, and Cushing's Syndrome.

"Antagonizing" refers to blocking the binding of an agonist at a receptor molecule or to inhibiting the signal produced by a receptor-agonist. A receptor antagonist blocks or dampens agonist-mediated responses.

"Therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

The present invention provides many fused azadecalin compounds. In some embodiments, the present invention provides compounds having the formula:

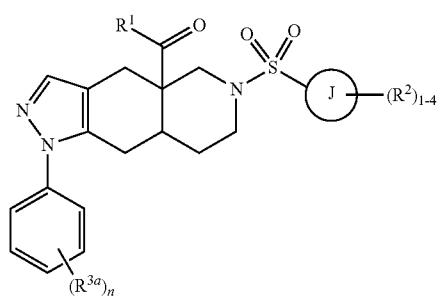

(I)

wherein $R^1$ of formula I is a heteroaryl ring having from 5 to 6 ring members and from 1 to 4 heteroatoms, which can each independently be N, O, or S, optionally substituted with 1-4 groups, which can each independently be $R^{1a}$. Each $R^{1a}$ of formula I can independently be hydrogen, $C_{1-6}$ alkyl, halogen, $C_{1-6}$ haloalkyl, $C_{1-6}$ alkoxy, $C_{1-6}$ haloalkoxy, N-oxide, or $C_{3-8}$ cycloalkyl. Ring J of formula I can be an aryl ring or a heteroaryl ring having from 5 to 6 ring members and from 1 to 4 heteroatoms, which can each independently be N, O, or S. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, or $C_{3-8}$ heterocycloalkyl having from 1 to 3 heteroatoms wherein each can independently be N, O, or S. Alternatively, two $R^2$ groups on adjacent ring atoms are combined to form a heterocycloalkyl ring having from 5 to 6 ring members and from 1 to 3 heteroatoms, which can each independently be N, O, or S, wherein the heterocycloalkyl ring is optionally substituted with from 1 to 3 $R^{2c}$ groups. $R^{2a}$, $R^{2b}$ and $R^{2c}$ of formula I can each independently be hydrogen or $C_{1-6}$ alkyl. Each $R^{3a}$ of formula I can independently be a halogen. Subscript n of formula I can be an integer from 0 to 3. The compounds of formula I can also be the salts and isomers thereof.

In some embodiments, wherein $R^1$ of formula I can be a heteroaryl ring having from 5 to 6 ring members and from 1 to 4 heteroatoms which can each independently be N, O, or S, optionally substituted with 1-3 groups each independently selected from $R^{1a}$. Each $R^{1a}$ of formula I can be hydrogen, $C_{1-6}$ alkyl, halogen, $C_{1-6}$ haloalkyl, $C_{1-6}$ alkoxy, $C_{1-6}$ haloalkoxy, or $C_{3-8}$ cycloalkyl. Ring J of formula I can be an aryl ring or a heteroaryl ring having from 5 to 6 ring members and from 1 to 3 heteroatoms which can each independently be N, O, or S. Each $R^2$ of formula I can independently be hydrogen, $C_{1-6}$ alkyl, halogen, $C_{1-6}$ haloalkyl, CN, —$NR^{2a}R^{2b}$, $C_{3-8}$ cycloalkyl, or $C_{3-8}$ heterocycloalkyl having from 1 to 3 heteroatoms which can each independently be N, O, or S. N, O, or S, wherein the heterocycloalkyl ring is optionally substituted with from 1 to 3 $R^{2c}$ groups. $R^{2a}$, $R^{2b}$ and $R^{2c}$ of formula I can each independently be hydrogen or $C_{1-6}$ alkyl. Each $R^{3a}$ can independently be halogen. Subscript n of formula I can be an integer from 0 to 3. The compounds of formula I can also be the salts and isomers thereof.

In some embodiments, $R^1$ can be a heteroaryl ring having from 5 to 6 ring members and from 1 to 3 heteroatoms which each can independently be N, O, or S, optionally substituted with 1-2 groups which can each independently be $R^{1a}$. Each $R^{1a}$ can independently be hydrogen, $C_{1-6}$ alkyl, halogen, or $C_{1-6}$ haloalkyl. Ring J can be an aryl ring or a heteroaryl ring having from 5 to 6 ring members and from 1 to 3 heteroatoms, which can independently be N or S. Each $R^2$ of formula I can independently be hydrogen, $C_{1-6}$ alkyl, halogen, $C_{1-6}$ haloalkyl or —CN. $R^{3a}$ can be F. Subscript n can be an integer from 0 to 1.

In some embodiments, $R^1$ can be a heteroaryl ring having from 5 to 6 ring members and from 1 to 3 heteroatoms which can each independently be N or S, optionally substituted with 1-2 groups which can each independently be $R^{1a}$. Each $R^{1a}$ can independently be hydrogen, $C_{1-6}$ alkyl, or $C_{1-6}$ haloalkyl. Ring J can be phenyl, pyridine, pyrazole, or triazole. Each $R^2$ can independently be hydrogen, $C_{1-6}$ alkyl, halogen, $C_{1-6}$ haloalkyl or —CN. $R^{3a}$ can be F.

In some embodiments, $R^1$ can be pyridine or thiazole. Ring J can be phenyl, pyridine, pyrazole, or triazole. Each $R^2$ can independently be hydrogen, $C_{1-6}$ alkyl, halogen, $C_{1-6}$ haloalkyl or —CN. $R^{3a}$ can be F. In some embodiments, $R^1$ can be 2-thiazole, 4-thiazole, 5-thiazole, 2-pyridine, 3-pyridine, or 4-pyridine. In some embodiments, R¹ can be 2-pyridine; 2-thiazole; or 4-thiazole. In some embodiments, R¹ can be pyridine. In some embodiments, R¹ can be triazole. In some embodiments, $R^{1a}$ can independently be hydrogen, $C_{1-6}$ alkyl, or $C_{1-6}$ haloalkyl. In some embodiments, $R^{1a}$ can independently be hydrogen, methyl, or trifluoromethyl.

In some embodiments, ring J can be phenyl, pyridine, pyrazole, or triazole. In some embodiments, ring J can be phenyl, 2-pyridine, 3-pyridine, 4-pyridine, 1-pyrazole, 3-pyrazole, 4-pyrazole, 5-pyrazole, 1,2,3-triazol-4-yl, 1,2,3,-triazol-5-yl, 1,2,4-triazol-3-yl, or 1,2,4-triazol-5-yl. In some embodiments, R² can independently be hydrogen, methyl, ethyl, propyl, isopropyl, F, Cl, or —CF₃.

The compounds of the present invention include at least one stereogenic center at the bridgehead carbon. Accordingly, the compounds can include a mixture of isomers, including enantiomers in a racemic mixture, or in enantiomerically pure mixtures that are substantially the R- or S-isomer. The compounds can also adopt a cis- or trans-conformation across the bridgehead carbons (carbons 4a and 8a) of the 4,4a,5,6,7,8,8a,9-octahydro-1H-pyrazolo[3,4-g]isoquinoline portion of the compounds. In some embodiments, the compounds of formula I can have the following structure:

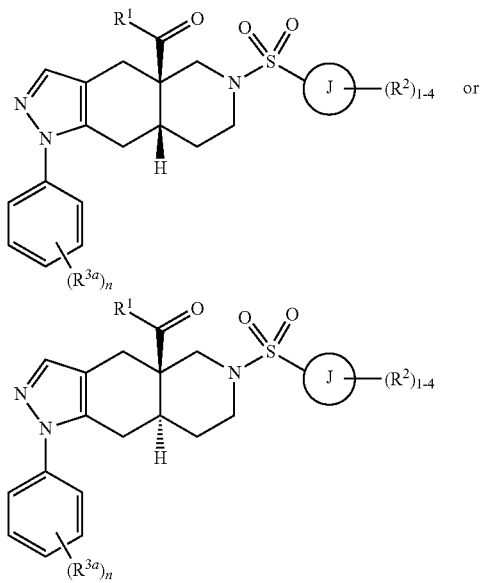

Any suitable heteroaryl can be used for R¹ in the compounds of the present invention, as defined in the definitions above. In some embodiments, the heteroaryl of R¹ can have from 5 to 6 ring members and from 1 to 4 heteroatoms which can each independently be N, O or S, optionally substituted with 1-4 groups which can each independently be $R^{1a}$. In some embodiments, the heteroaryl of R¹ can have from 5 to 6 ring members and from 1 to 3 heteroatoms which can each independently be N, O or S, optionally substituted with 1-4 groups which can each independently be $R^{1a}$. In some embodiments, the heteroaryl of R¹ can have from 5 to 6 ring members and from 1 to 2 heteroatoms which can each independently be N, O or S, optionally substituted with 1-4 groups which can each independently be $R^{1a}$. In some embodiments, the heteroaryl of R¹ can have from 5 to 6 ring members and from 1 to 2 heteroatoms which can each independently be N or S, optionally substituted with 1-4 groups which can each independently be $R^{1a}$.

In some embodiments, the heteroaryl of R¹ can be pyrrole, pyrazole, imidazole, triazole, tetrazole, furan, oxazole, isoxazole, oxadiazole, thiophene, thiazole, isothiazole, thiadiazole, pyridine, pyrazine, pyrimidine, or pyridazine. In some embodiments, the heteroaryl of R¹ can be 2-pyrrole, 3-pyrrole, 1-pyrazole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 1,2,3,4-tetrazol-1-yl, 1,2,3,4,tetrazol-5-yl, 2-furan, 3-furan, 2-oxazole, 4-oxazole, 5-oxazole, 3-isoxazole, 4-isooxazole, 5-isooxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 3-isothiazole, 4-isothiazole, 5-isothiazole, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,3,4-thiadiazol-2-yl, 2-pyridine, 3-pyridine, 4-pyridine, pyrazine, 2-pyrimidine, 4-pyrimidine, 5-pyrimidine, 6-pyrimidine, 3-pyridazine, 4-pyridazine, 5-pyridazine, or 6-pyridazine. In some embodiments, the heteroaryl of R¹ can be pyrazole, imidazole, triazole, furan, oxazole, oxadiazole, thiophene, thiazole, pyridine, pyrazine, pyrimidine or pyrimidine. In some embodiments, the heteroaryl of R¹ can be imidazole, furan, oxazole, oxadiazole, thiophene, thiazole, or pyridine. In some embodiments, the heteroaryl of R¹ can be 1-pyrazole, 3-pyrazole, 4-pyrazole, 5-pyrazole, 2-imidazole, 4-imidazole, 5-imidazole, 1,2,3-triazol-4-yl, 1,2,3,-triazol-5-yl, 1,2,4-triazol-3-yl, 1,2,4-triazol-5-yl, 2-furan, 3-furan, 2-oxazole, 4-oxazole, 5-oxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 2-pyridine, 3-pyridine, 4-pyridine, pyrazine, 2-pyrimidine, 4-pyrimidine, 5-pyrimidine, or 6-pyrimidine. In some embodiments, the heteroaryl of R¹ can be 3-pyrazole, 4-pyrazole, 2-imidazole, 1,2,4-triazol-5-yl, 2-furan, 2-oxazole, 4-oxazole, 1,3,4-oxadiazol-2-yl, 2-thiophene, 2-thiazole, 4-thiazole, 5-thiazole, 2-pyridine, 3-pyridine, 4-pyridine, pyrazine, or 2-pyrimidine. In some embodiments, the heteroaryl of R¹ can be 2-imidazole, 4-imidazole, 5-imidazole, 2-furan, 3-furan, 2-oxazole, 4-oxazole, 5-oxazole, 1,2,4-oxadiazol-3-yl, 1,2,4-oxadiazol-5-yl, 1,2,5-oxadiazol-3-yl, 1,3,4-oxadiazol-2-yl, 2-thiophene, 3-thiophene, 2-thiazole, 4-thiazole, 5-thiazole, 2-pyridine, 3-pyridine, or 4-pyridine.

In some embodiments, the heteroaryl of R¹ can be pyridine or thiazole. In some embodiments, the heteroaryl of R¹ can be 2-thiazole, 4-thiazole, 5-thiazole, 2-pyridine, 3-pyridine, or 4-pyridine. In some embodiments, the heteroaryl of R¹ can be 2-thiazole, 4-thiazole or 2-pyridine. In some embodiments, the heteroaryl of R¹ can be pyridine. In some embodiments, the heteroaryl of R¹ can be thiazole.

In some embodiments, the heteroaryl of R¹ can be optionally substituted with 1-4 groups which can each independently be $R^{1a}$. In some embodiments, each $R^{1a}$ can independently be hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, or $C_{3-8}$ heterocycloalkyl. In some embodiments, each $R^{1a}$ can independently be hydrogen, $C_{1-6}$ alkyl, $C_{1-6}$ haloalkyl, $C_{1-6}$ alkoxy or $C_{3-8}$ heterocycloalkyl. In some embodiments, each $R^{1a}$ can independently be hydrogen, $C_{1-6}$ alkyl, $C_{1-6}$ haloalkyl, or $C_{1-6}$ alkoxy. In some embodiments, each $R^{1a}$ can independently be hydrogen, $C_{1-6}$ alkyl, or $C_{1-6}$ haloalkyl. In some embodiments, each $R^{1a}$ can independently be hydrogen or $C_{1-6}$ alkyl. The alkyl of $R^{1a}$ can be any suitable alkyl group, such as methyl, ethyl, propyl, butyl, pentyl, and hexyl, among others. In some embodiments, each $R^{1a}$ can independently be hydrogen, methyl, ethyl, trifluoromethyl, methoxy, or pyrrolidinyl. In some embodiments, each $R^{1a}$ can independently be hydrogen, methyl, or trifluoromethyl. In some embodiments, each $R^{1a}$ can independently be hydrogen or methyl.

In some embodiments, the heteroaryl of $R^1$ can be 3-pyrazole, 4-pyrazole, 2-imidazole, 1,2,4-triazol-5-yl, 2-furan, 2-oxazole, 4-oxazole, 1,3,4-oxadiazol-2-yl, 2-thiophene, 2-thiazole, 4-thiazole, 5-thiazole, 2-pyridine, 3-pyridine, 4-pyridine, pyrazine, or 2-pyrimidine, and Ring J can be 2-pyridine, 3-pyridine, 4-pyridine, imidazol-2-yl, imidazol-4-yl, imidazol-5-yl, pyrazol-3-yl, pyrazol-4-yl, pyrazol-5-yl, 1,2,3-triazol-4-yl, 1,2,3-triazol-5-yl, or isoxazol-4-yl.

Ring J of formula I can be any suitable ring. In some embodiments, ring J of formula I can be a cycloalkyl ring, a heterocycloalkyl ring, an aryl ring or a heteroaryl ring, wherein the heterocycloalkyl and heteroaryl rings can have from 5 to 6 ring members and from 1 to 4 heteroatoms which can each independently be N, O or S. In some embodiments, ring J can be heterocycloalkyl, aryl or heteroaryl. Suitable heterocycloalkyl groups include those defined in the definitions above. In some embodiments, the heterocycloalkyl can tetrahydrofuran. Suitable aryl groups for ring J include those defined in the definitions above. Representative aryl groups include phenyl and naphthyl. In some embodiments, the aryl group of ring J can be phenyl. Suitable heteroaryl groups for ring J include those defined in the definitions above. Representative heteroaryl groups include pyrrole, pyridine, imidazole, pyrazole, triazole, tetrazole, pyrazine, pyrimidine, pyridazine, triazine (1,2,3-, 1,2,4- and 1,3,5- isomers), thiophene, furan, thiazole, isothiazole, oxazole, and isoxazole. In some embodiments, the heteroaryl can be pyridyl or thiophene. In some embodiments, ring J can be aryl or heteroaryl. In some embodiments, ring J can be phenyl, pyridine, imidazole, pyrazole, triazole, tetrazole, thiadiazole, isothiazole, or isoxazole. In some embodiments, ring J can be phenyl, pyridine, pyrazole or triazole. In some embodiments, ring J can be phenyl, 2-pyridine, 3-pyridine, 4-pyridine, 1-pyrazole, 3-pyrazole, 4-pyrazole, 5-pyrazole, 1,2,3-triazol-4-yl, 1,2,3,-triazol-5-yl, 1,2,4-triazol-3-yl, and 1,2,4-triazol-5-yl. In some embodiments, ring J can be phenyl. In some embodiments, ring J can be pyridine. In some embodiments, ring J can be pyrazole. In some embodiments, ring J can be triazole.

Ring J of formula I can be substituted with any suitable number of $R^2$ groups. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —NR$^{2a}$R$^{2b}$, —C(O)R$^{2a}$, —C(O)OR$^{2a}$, —C(O)NR$^{2a}$R$^{2b}$, —SR$^{2a}$, —S(O)R$^{2a}$, —S(O)$_2$R$^{2a}$, $C_{3-8}$ cycloalkyl, or $C_{3-8}$ heterocycloalkyl, wherein the heterocycloalkyl groups are optionally substituted with 1-4 $R^{2c}$ groups. In some embodiments, each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —NR$^{2a}$R$^{2b}$, —C(O)OR$^{2a}$, —S(O)$_2$R$^{2a}$, $C_{3-8}$ cycloalkyl, or $C_{3-8}$ heterocycloalkyl, wherein the heterocycloalkyl group has 5-6 ring members and 1 to 2 heteroatoms. In some embodiments, each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —NR$^{2a}$R$^{2b}$, —S(O)$_2$R$^{2a}$, $C_{3-8}$ cycloalkyl, or $C_{3-8}$ heterocycloalkyl, wherein the heterocycloalkyl group has 5-6 ring members and 1 to 2 heteroatoms. Each $R^2$ of formula I can independently be hydrogen, $C_{1-6}$ alkyl, halogen, $C_{1-6}$ haloalkyl, $C_{1-6}$ alkoxy, $C_{1-6}$ haloalkoxy, —CN, —NR$^{2a}$R$^{2b}$, $C_{3-8}$ cycloalkyl, or $C_{3-8}$ heterocycloalkyl, wherein the heterocycloalkyl groups are optionally substituted with 1-4 $R^{2c}$ groups. In some embodiments, each $R^2$ can independently be hydrogen, halogen, $C_{1-6}$ haloalkyl, —CN, or heterocycloalkyl having 5-6 ring members and 1 to 2 heteroatoms wherein at least one heteroatom is N. Heterocycloalkyl groups having 5-6 ring members and 1 to 2 heteroatoms with at least one nitrogen include, but are not limited to, pyrrolidine, piperidine, pyrazolidine, imidazolidine, piperazine (1,2-, 1,3- and 1,4-isomers), oxazolidine, isoxalidine, thiazolidine, isothiazolidine, morpholine, or thiomorpholine. In some embodiments, each $R^2$ can independently be hydrogen, methyl, ethyl, propyl, isopropyl, F, Cl, —CF$_3$, CH$_2$OMe, OMe, OCHF$_2$, —CN, —NMe$_2$, —C(O)OH, —C(O)NMe$_2$, —S(O)$_2$Me, pyrrolidine, piperidine or morpholine. In some embodiments, each $R^2$ can independently be hydrogen, methyl, ethyl, F, Cl, —CF$_3$, OMe, OCHF$_2$, —CN, —NMe$_2$, —S(O)$_2$Me, pyrrolidine, piperidine or morpholine. In some embodiments, each $R^2$ can independently be hydrogen, methyl, ethyl, n-propyl, isopropyl, F, Cl, and —CF$_3$. In some embodiments, $R^2$ can be —CF$_3$. Ring J can be substituted with 1, 2, 3 or 4 $R^2$ groups. In some embodiments, ring J is substituted with 1 $R^2$ group.

Alternatively, two $R^2$ groups on adjacent atoms of Ring J can be combined to form a heterocycloalkyl ring having from 5 to 6 ring members and from 1 to 3 heteroatoms that can each be N, O or S, wherein the heterocycloalkyl ring is optionally substituted with from 1 to 3 $R^{2c}$ groups. When two $R^2$ groups are combined, any suitable heterocycloalkyl groups can be formed. In some embodiments, the heterocycloalkyl formed by the combination of two $R^2$ groups can have 6 ring members and from 1 to 2 heteroatoms that can each be N, O or S. In some embodiments, the heterocycloalkyl formed by the combination of two $R^2$ groups can have 6 ring members and from 1 to 2 heteroatoms that can each be N or O. In some embodiments, the heterocycloalkyl formed by the combination of two $R^2$ groups can have 6 ring members and 2 heteroatoms that can each be N or O. In some embodiments, the heterocycloalkyl formed by the combination of two $R^2$ groups can be morpholine. When ring J is pyridine and the heterocycloalkyl formed by the combination of two $R^2$ groups, the combination can be any suitable pyrido-oxazine such as 3,4-dihydro-2H-pyrido[3,2-b][1,4]oxazin-7-yl. And when the two $R^2$ groups are combined to form a heterocycloalkyl, the heterocycloalkyl can be substituted with from 1 to 3 $R^{2c}$ groups such as H or Me.

Several $R^2$ groups can be further substituted with one or more of $R^{2a}$ and $R^{2b}$. $R^{2a}$ and $R^{2b}$ can each independently be hydrogen or $C_{1-6}$ alkyl.

Each $R^{3a}$ can be any halogen. In some embodiments, each $R^{3a}$ group can independently be F, I, Cl, or Br. In some embodiments, $R^{3a}$ can be F. The $R^{3a}$ group can be present at any position on the phenyl ring to form a 2-, 3- or 4-substituted ring. In some embodiments, the phenyl ring is substituted at the 4-position.

Subscript n of formula I can be an integer from 0 to 3. In some embodiments, subscript n can be 0, 1, 2, or 3. In some embodiments, subscript n can be 0 or 1. In some embodiments, subscript n can be 0. In some embodiments, subscript n can be 1.

When R³ᵃ of formula I is 4-fluoro, the compounds of the present invention can have the following structure:

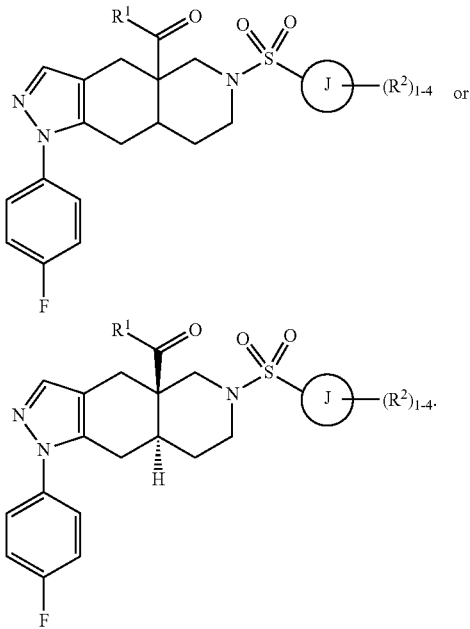

In some embodiments, the compound of formula I can be:
- ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-6-((3,4-dichlorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone,
- ((4aR,8aS)-6-((3,4-difluorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(thiazol-2-yl)methanone,
- ((4aR,8aS)-1-(4-fluorophenyl)-6-((3-fluorophenyl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((3-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((1-methyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((1-methyl-1H-pyrazol-3-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((1-methyl-1H-pyrazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-6-((1-ethyl-1H-pyrazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-6-((1-ethyl-1H-pyrazol-5-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(thiazol-2-yl)methanone,
- ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((1-methyl-1H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-methylpyridin-2-yl)methanone,
- ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone,
- 3-(((4aR,8aS)-1-(4-fluorophenyl)-4a-picolinoyl-4a,5,7,8,8a,9-hexahydro-1H-pyrazolo[3,4-g]isoquinolin-6(4H)-yl)sulfonyl)benzonitrile,
- ((4aR,8aS)-6-((3-fluoro-4-(trifluoromethyl)phenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((4-methyl-3,4-dihydro-2H-pyrido[3,2-b][1,4]oxazin-7-yl)sulfonyl)-4,4a,5,6,7,8,8a,9-octahydro-1H-pyrazolo[3,4-g]isoquinolin-4a-yl)(pyridin-2-yl)methanone,
- ((4aR,8aS)-1-(4-fluorophenyl)-6-((1-propyl-1H-1,2,3-triazol-5-yl)sulfonyl)-4,4a,5,6,7,8,8a,9-octahydro-1H-pyrazolo[3,4-g]isoquinolin-4a-yl)(thiazol-2-yl)methanone,
- ((4aR,8aS)-1-(4-fluorophenyl)-6-((1-methyl-1H-1,2,3-triazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
- ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone,
- ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((1-isopropyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-6-((2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((1-isopropyl-1H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-4-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone, or ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(thiazol-4-yl)methanone.

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2H$), tritium (H), iodine-125 ($^{125}I$), carbon-13 ($^{13}C$), or carbon-14 ($^{14}C$). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Compounds of the present invention can be prepared as shown in FIG. 1. Starting materials can be obtained from commercial sources, by employing known synthetic methods, and by employing methods described in U.S. Pat. No. 7,928,237, incorporated herein by reference. Esters I are converted to ketones IV by reaction with an appropriate organometallic reagent such as a Grignard reagent, an organolithium reagent, an organoboron reagent, an organocerium reagent or an organozinc reagent in a solvent such as ether or tetrahydrofuran, or a similar aprotic solvent. Preferably, the reaction is carried out by using an aryl lithium reagent in a solvent such as ether or tetrahydrofuran. It may be advantageous to carry out the reaction at reduced temperature. Ketones of formula IV are also prepared by reaction of an aldehyde of formula II with an appropriate organometallic reagent followed by oxidation of the resultant alcohols of formula III with a suitable oxidizing agent such as the Dess-Martin periodinane reagent in an inert solvent such as dichloromethane. The tert-butoxycarbonyl protecting group is removed from IV by treatment with an acid, such as HCl, HBr, trifluoroacetic acid, p-toluenesulfonic acid or methanesulfonic acid, preferably HCl or trifluoroacetic acid, optionally in a solvent such as dioxane, dichloromethane, ethanol or tetrahydrofuran, either under anhydrous or aqueous conditions. Preferably, the reaction is carried out using either HCl in dioxane, or trifluoroacetic acid in dichloromethane. Amines V are converted to the compounds of formula (1) by treatment with an appropriate substituted sulfonyl halide, such as the sulfonyl chloride VI, in an inert solvent such as dichloromethane, toluene or tetrahydrofuran, preferably dichloromethane, in the presence of a base such as N,N-di-isopropylethylamine or triethylamine. It may be convenient to carry out the sulfonylation reaction in situ, without isolation of the amine V. Compounds of formula (1) can also be prepared from amines of formula V in a two-step sequence beginning with reaction of amines V with a halo-substituted sulfonyl chloride, VII, to afford a halo-substituted sulfonamide derivative exemplified by VIII (in which X represents a halogen). The halogen substituent X can be converted in a substituent $R^2$ by any standard method known to those skilled in the art.

Figure 2:
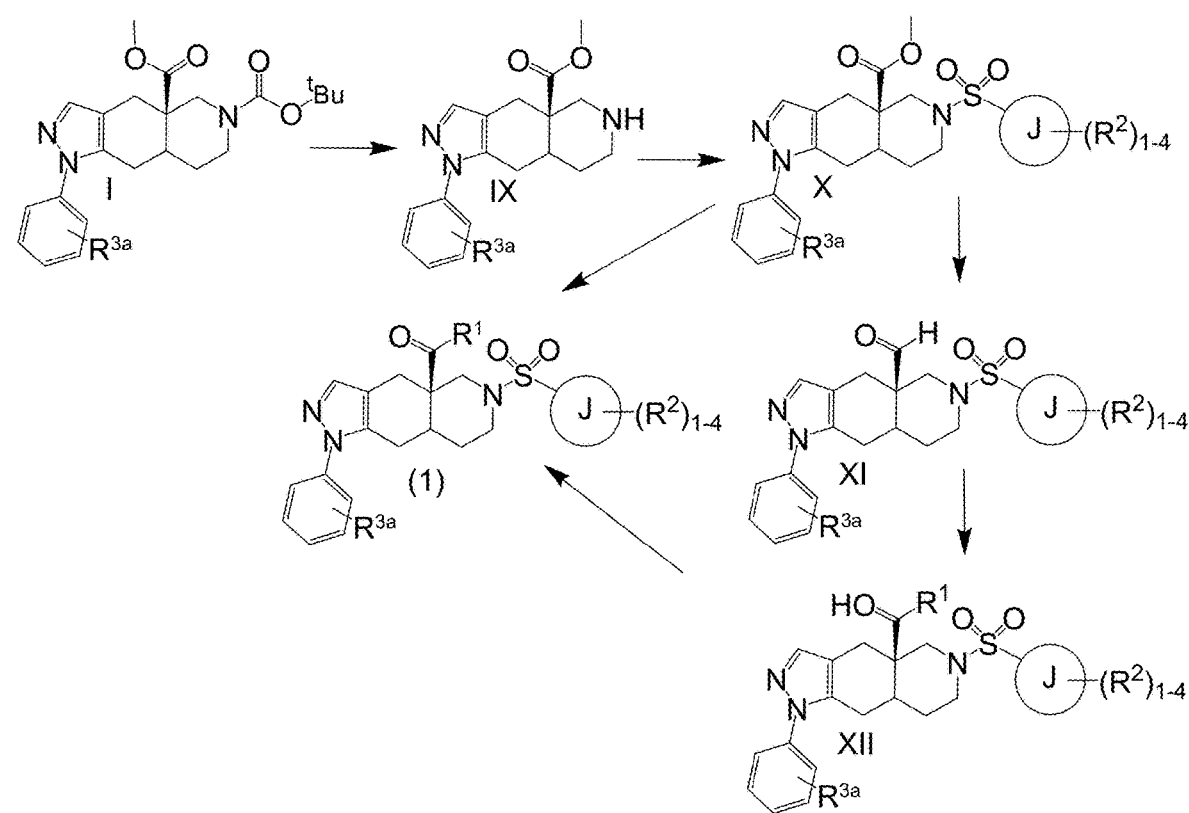

Alternatively, compounds of formula (1) are prepared as shown FIG. 2. The tert-butoxycarbonyl protecting group is removed from I by treatment with an acid, such as HCl, HBr, trifluoroacetic acid, p-toluenesulfonic acid or methanesulfonic acid, preferably HCl or trifluoroacetic acid, optionally in a solvent such as dioxane, dichloromethane, ethanol or tetrahydrofuran, either under anhydrous or aqueous conditions. Preferably, the reaction is carried out using either HCl in dioxane, or trifluoroacetic acid in dichloromethane. Amines IX are converted to the sulfonamides of formula X as described for the conversion of amines of formula V into sulfonamides of formula (1). The ester group in compounds of formula X is converted to an aldehyde of formula XI by using a reducing agent such as DIBAL-H, LiAlH$_4$ or RED-AL, preferably DIBAL-H in an inert solvent such as dichloromethane, tetrahydrofuran, benzene or toluene, preferably dichloromethane. It may be convenient to convert X into XI using a two-step process involving reduction of the ester to an alcohol and subsequent oxidation of the alcohol to an aldehyde of formula XI. The oxidation can be carried out using any suitable procedure, such as the Swern reaction, or an oxidizing reagent such as the Dess-Martin periodinane reagent in a suitable solvent, such as dichloromethane. Aldehydes of formula XI are converted into alcohols of formula XII using a suitable organometallic reagent, such as a Grignard reagent, an organolithium reagent, an organoboron reagent, an organocerium reagent or an organozinc reagent. Alcohols of formula XII are converted into ketones of formula (1) by oxidation. Suitable oxidation conditions include the Swern reaction and the use of the Dess-Martin periodinane reagent. Alternatively, esters of formula X are converted directly to ketones of formula (1) using an appropriate organometallic reagent, preferably an aryl lithium reagent in a suitable solvent, such as ether or tetrahydrofuran.

Figure 3:
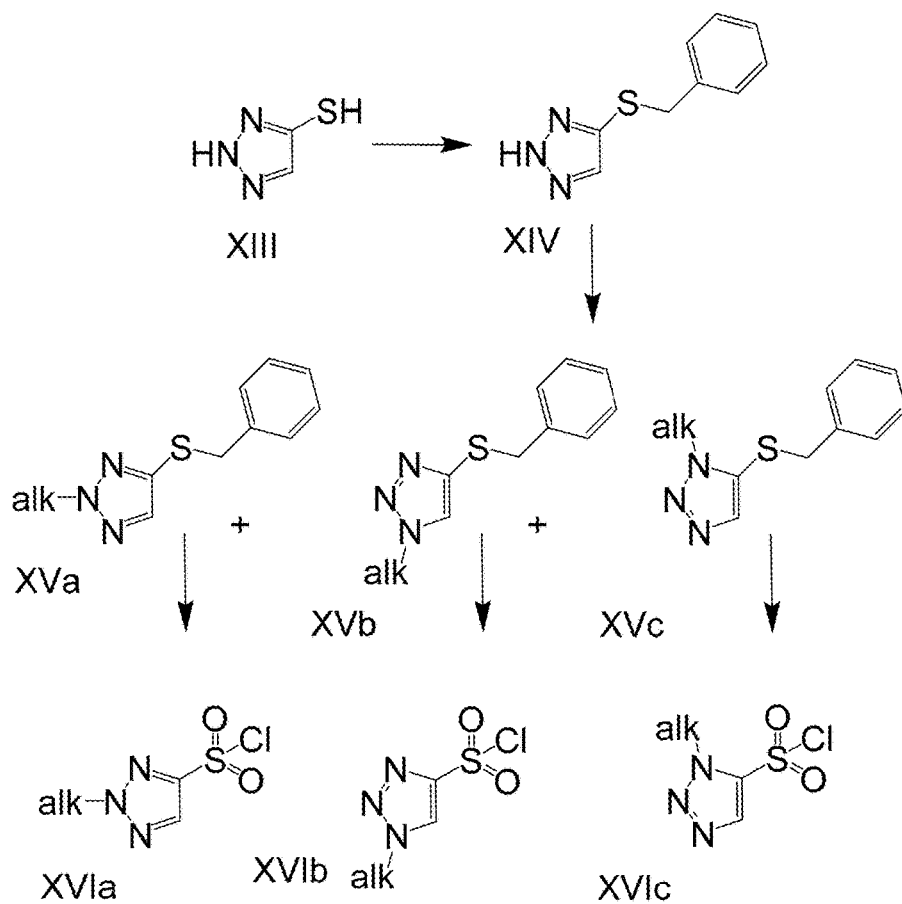
Figure 4:
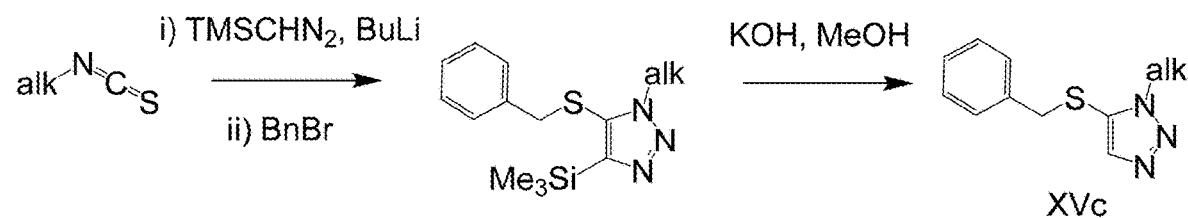

Compounds of formula I in which J represents a triazole and $R^2$ represents alkyl require the synthesis of the appropriate triazole sulfonyl chloride. The triazole sulfonyl chlorides employed in the current invention may be prepared by any suitable method known to those skilled in the art, such as the method depicted in FIG. 3. In FIG. 3, alk represents an alkyl group. The commercially available triazole thiol XIII is converted into a suitably protected thiol, such as the benzylthio triazole XIV, using any suitable conditions known to those skilled in the art. Preferably, thiol XIII is treated with benzyl bromide in a suitable solvent, such as ethanol. Alkylation of a protected thiol, such as benzyl thiol XIV provides a mixture of three regioisomeric alkyl pyrazoles XVa, XVb and XVc. The exact ratio of the products depends on the conditions used for the alkylation reaction. For example, the use of an appropriate alkyl iodide in N,N-dimethylformamide in the presence of potassium carbonate provides triazole XVa as the major product. The regiochemistry of the alkylated triazoles is determined using any suitable method known to those skilled in the art. For example, regiochemistry may be assigned by comparison with information in the scientific literature, by undertaking NOE experiments, by chemical manipulation to provide compounds of known structure, or by comparison with samples made by an alternative, unambiguous synthetic route. For example, the synthetic route depicted in FIG. 4 specifically provides triazole sulfides of formula XVc. In FIG. 4, alk represents an alkyl group.

Triazoles of formula XV are converted into sulfonyl chlorides of formula XVI using any appropriate method known to those skilled in the art. For example, oxidative cleavage of the thiobenzyl group using a suitable oxidizing agent may be employed. The use of N-chlorosuccinimide or chlorine gas, in a suitable solvent such as acetic acid, provides sulfonyl chlorides of formula XVI.

IV. Pharmaceutical Compositions

In some embodiments, the present invention provides a pharmaceutical composition including a compound of the present invention and a pharmaceutically acceptable excipient.

A. Formulation

The compositions of the present invention can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

B. Administration

The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compounds and compositions of the present invention, and any other agents, can be present in any suitable amount, and can depend on various factors including, but not limited to, weight and age of the subject, state of the disease, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

V. Method of Modulating a Glucocorticoid Receptor and Treating a Disorder

In some embodiments, the present invention provides a method of modulating a glucocorticoid receptor including contacting a glucocorticoid receptor with a compound of the present invention, thereby modulating the glucocorticoid receptor.

In some embodiments, the present invention provides a method of treating a disorder through antagonizing a glucocorticoid receptor, including administering to a subject in need thereof, a therapeutically effective amount of a compound of the present invention, thereby treating the disorder.

In some other embodiments, the present invention provides a method of treating a disorder through antagonizing a glucocorticoid receptor, the method including administering to a subject in need of such treatment, an effective amount of the compound of the present invention, thereby treating the disorder.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for other nuclear receptor. In another embodiment, the specific glucocorticoid receptor antagonist binds to the GR with an association constant ($K_d$) that is at least 100-fold less than the $K_d$ for the other nuclear receptor. In another embodiment, the specific glucocorticoid receptor antagonist binds to the GR with an association constant ($K_d$) that is at least 1000-fold less than the $K_d$ for the other nuclear receptor.

Examples of disorders or conditions suitable for use with present invention include, but are not limited to, obesity, diabetes, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, Huntington's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress disorder, post-surgical bone fracture, medical catabolism, major psychotic depression, mild cognitive impairment, psychosis, dementia, hyperglycemia, central serous retinopathy, alcohol dependence, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, migraine headaches, and cancers such as ovarian, breast and prostate cancer. In some embodiments, the disorder or condition can be major psychotic depression, stress disorders or antipsychotic induced weight gain. In other embodiments, the disorder or condition can be Cushing's Syndrome.

A. Binding Assays

GR modulators of this invention can be tested for binding activity in a variety of assays. For example, by screening for the ability to compete with a GR ligand, such as dexamethasone, for binding to the glucocorticoid receptor. Those of skill in the art will recognize that there are a number of ways to perform such competitive binding assays. In some embodiments, GR is pre-incubated with a labeled GR ligand and then contacted with a test compound. This type of competitive binding assay may also be referred to herein as a binding displacement assay. Alteration (e.g., a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Terr ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3$H, $^{125}$I, $^{35}$S, $^{14}$C, or $^{32}$P. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

B. Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Typically, compounds that are tested in whole-cell assays are also tested in a cytotoxicity assay. Cytotoxicity assays are used to determine the extent to which a perceived modulating effect is due to non-GR binding cellular effects. In an exemplary embodiment, the cytotoxicity assay includes contacting a constitutively active cell with the test compound. Any decrease in cellular activity indicates a cytotoxic effect.

C. Specificity

The compounds of the present invention may be subject to a specificity assay (also referred to herein as a selectivity assay). Typically, specificity assays include testing a compound that binds GR in vitro or in a cell-based assay for the degree of binding to non-GR proteins. Selectivity assays may be performed in vitro or in cell based systems, as described above. Binding may be tested against any appropriate non-GR protein, including antibodies, receptors, enzymes, and the like. In an exemplary embodiment, the non-GR binding protein is a cell-surface receptor or nuclear receptor. In another exemplary embodiment, the non-GR protein is a steroid receptor, such as estrogen receptor, progesterone receptor, androgen receptor, or mineralocorticoid receptor.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

VI. Examples

Structures are named according to standard IUPAC nomenclature using the CambridgeSoft ChemDraw naming package.

$^1$H NMR spectra were recorded at ambient temperature using a Bruker Avance III spectrometer (400 MHz).

Mass spectrometry (LCMS) experiments to determine retention times and associated mass ions were performed as follows: experiments were performed using an Agilent Infinity 1260 LC 6120 quadrupole mass spectrometer with positive and negative ion electrospray and ELS/UV @ 254 nm detection using an Agilent Zorbax Extend C18, Rapid Resolution HT 1.8 micron C18 30×4.6 mm column and a 2.5 mL/minute flow rate. The initial solvent system was 95% water containing 0.1% formic acid (solvent A) and 5% acetonitrile containing 0.1% formic acid (solvent B) ramping up to 5% solvent A and 95% solvent B over the next 3.0 minutes, the flow rate was then increased to 4.5 mL/minute and held for 0.5 minutes at 95% B. Over 0.1 minute the gradient was returned to 95% A and 5% B and 3.5 mL/minute and was held at these conditions for 0.3 minutes; the final 0.1 minute resulted in the return to the initial starting conditions, 95% A 5% B at 2.5 mL/minute.

Intermediate 1A. (4aR,8aS)-methyl 1-(4-fluorophenyl)-6-((4-(trifluoromethyl)phenyl)sulfonyl)-4,4a,5,6,7,8,8a,9-octahydro-1H-pyrazolo[3,4-g]isoquinoline-4a-carboxylate

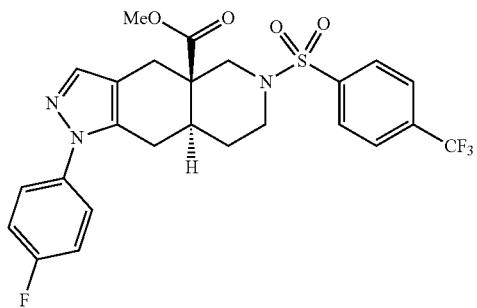 [SMILES: COC(=O)[C@]12Cc3cnn(-c4ccc(F)cc4)c3C[C@@H]1CCN(S(=O)(=O)c1ccc(C(F)(F)F)cc1)C2]

A solution of (4aR,8aS)-6-tert-butyl 4a-methyl 1-(4-fluorophenyl)-4a,5,7,8,8a,9-hexahydro-1H-pyrazolo[3,4-g]isoquinoline-4a,6(4H)-dicarboxylate (WO 2005087769; 0.35 g, 0.815 mmol) in HCl (4M solution in dioxane) (4.07 ml, 16.30 mmol) was stirred at room temperature for 1 hour, then solvent was evaporated to give a white solid. This material was dissolved in dichloromethane (10 ml), and Hunig's Base (0.712 ml, 4.07 mmol), then 4-(trifluoromethyl)benzene-1-sulfonyl chloride (0.239 g, 0.978 mmol) were added. The reaction mixture was stirred at room temperature for 4 days, before solvent was evaporated, and the crude product was purified by column chromatography on silica gel (gradient: 20-40% ethyl acetate in isohexane) to afford (4aR,8aS)-methyl 1-(4-fluorophenyl)-6-((4-(trifluoromethyl)phenyl)sulfonyl)-4,4a,5,6,7,8,8a,9-octahydro-1H-pyrazolo[3,4-g]isoquinoline-4a-carboxylate (0.38 g) as a colourless gum, LCMS: RT 2.66 min, m+H=538.0.

The following intermediates were similarly prepared from appropriate starting materials:

Intermediate 1B. (4aR,8aS)-methyl 6-((3,4-dichlorophenyl)sulfonyl)-1-(4-fluorophenyl)-4,4a,5,6,7,8,8a,9-octahydro-1H-pyrazolo[3,4-g]isoquinoline-4a-carboxylate

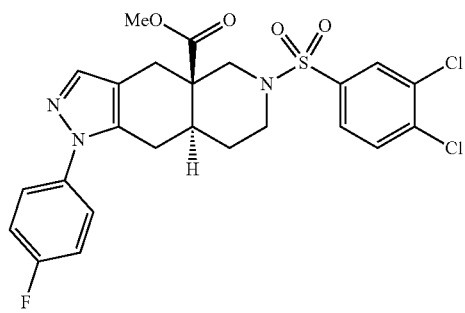 [SMILES: COC(=O)[C@]12Cc3cnn(-c4ccc(F)cc4)c3C[C@@H]1CCN(S(=O)(=O)c1ccc(Cl)c(Cl)c1)C2]

LCMS: RT 3.12 min, m+H=538.1/540.1

Intermediate 1C. (4aR,8aS)-methyl 6-((3,4-difluorophenyl)sulfonyl)-1-(4-fluorophenyl)-4,4a,5,6,7,8,8a,9-octahydro-1H-pyrazolo[3,4-g]isoquinoline-4a-carboxylate

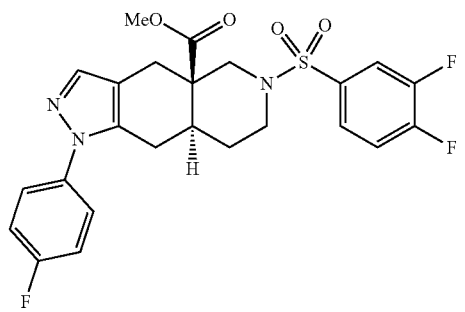 [SMILES: COC(=O)[C@]12Cc3cnn(-c4ccc(F)cc4)c3C[C@@H]1CCN(S(=O)(=O)c1ccc(F)c(F)c1)C2]

LCMS: RT 2.80 min, m+H=506.0.

Intermediate 2A. (4aR,8aS)-tert-butyl 1-(4-fluorophenyl)-4a-picolinoyl-4a,5,7,8,8a,9-hexahydro-1H-pyrazolo[3,4-g]isoquinoline-6(4H)-carboxylate

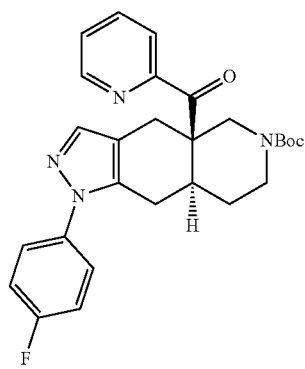 [SMILES: CC(C)(C)OC(=O)N1CC[C@H]2Cc3c(cnn3-c3ccc(F)cc3)C[C@]2(C(=O)c2ccccn2)C1]

2-Bromopyridine (0.690 ml, 7.10 mmol) in dry tetrahydrofuran (5 ml) was added to butyllithium (2.5M in hexanes) (2.91 ml, 7.28 mmol) in dry tetrahydrofuran (3 ml) at −78° C. The reaction mixture was stirred at −78° C. for 45 minutes. A solution of (4aR,8aS)-6-tert-butyl 4a-methyl 1-(4-fluorophenyl)-4a,5,7,8,8a,9-hexahydro-1H-pyrazolo[3,4-g]isoquinoline-4a,6(4H)-dicarboxylate (1.0 g, 2.328 mmol) in dry tetrahydrofuran (8 ml) was added dropwise and the reaction mixture was stirred for 45 minutes at −78° C. Water (10 ml) was added and the reaction mixture was stirred at room temperature for 10 minutes. The aqueous phase was extracted with ethyl acetate (2×10 ml). The combined organic phases were washed with brine (10 ml), dried (magnesium sulfate), and the solvent removed to give a brown oil. The crude product was purified by column chromatography on silica gel (gradient: 10-70% ethyl acetate in isohexane) to afford (4aR,8aS)-tert-butyl 1-(4-fluorophenyl)-4a-picolinoyl-4a,5,7,8,8a,9-hexahydro-1H-pyrazolo[3,4-g]isoquinoline-6(4H)-carboxylate (766 mg) as a pale yellow solid, LCMS: RT 2.70 min, m+H=477.

The following intermediates were similarly prepared from appropriate starting materials:

Intermediate 2B. (4aR,8aS)-tert-butyl 1-(4-fluorophenyl)-4a-(4-(trifluoromethyl)picolinoyl)-4a,5,7,8,8a,9-hexahydro-1H-pyrazolo[3,4-g]isoquinoline-6(4H)-carboxylate Intermediate 2C. (4aR,8aS)-tert-butyl 1-(4-fluorophenyl)-4a-(thiazole-2-carbonyl)-4a,5,7,8,8a,9-hexahydro-1H-pyrazolo[3,4-g]isoquinoline-6(4H)-carboxylate

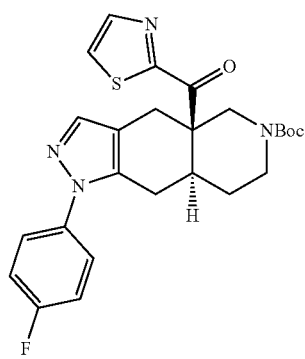

Using diethyl ether as solvent in place of tetrahydrofuran. LCMS: RT 2.67 min, m+H=482.9.

Intermediate 2D. (R)-tert-butyl 1-(4-fluorophenyl)-4a-(4-methylpicolinoyl)-4a,5,7,8,8a,9-hexahydro-1H-pyrazolo[3,4-g]isoquinoline-6(4H)-carboxylate

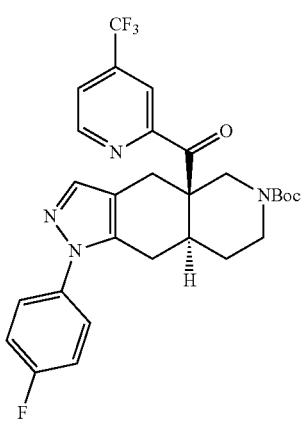 [SMILES: CC(C)(C)OC(=O)N1CC[C@H]2Cc3c(cnn3-c3ccc(F)cc3)C[C@]2(C(=O)c2cc(C(F)(F)F)ccn2)C1]

LCMS: RT 2.88 min, m+H=545.3.

LCMS: RT 2.77 min, m+H=491.3.

Intermediate 2E. (R)-tert-butyl 1-(4-fluorophenyl)-4a-(thiazole-5-carbonyl)-4a,5,7,8,8a,9-hexahydro-1H-pyrazolo[3,4-g]isoquinoline-6(4H)-carboxylate

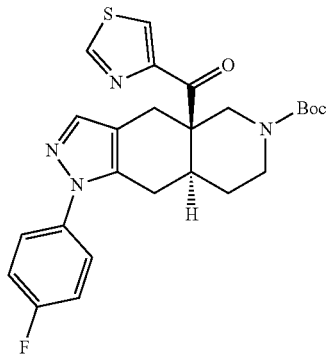 [SMILES: CC(C)(C)OC(=O)N1CC[C@H]2Cc3c(cnn3-c3ccc(F)cc3)C[C@]2(C(=O)c2cscn2)C1]

Using diethyl ether as solvent in place of tetrahydrofuran. LCMS: RT 2.51 min, m+H=483.2.

Intermediate 3A. 4-(benzylthio)-1H-1,2,3-triazole

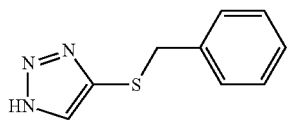 [SMILES: c1ccc(CSc2c[nH]nn2)cc1]

Benzyl bromide (11.79 ml, 99 mmol) was added dropwise to a solution of sodium 1H-1,2,3-triazole-4-thiolate (12.2 g, 99 mmol) in ethanol (100 ml) at 0° C. The reaction mixture was allowed to warm to room temperature and stirred for 20 minutes. The reaction mixture was diluted with ethyl acetate (100 ml) and washed with water (100 ml), brine (100 ml) and dried (sodium sulfate). The solvent was removed to give 4-(benzylthio)-1H-1,2,3-triazole (16.9 g) as a white solid, LCMS: RT 1.66 min, m+H=191; 1H NMR (400 MHz, CDCl$_3$): δ 9.72 (1H, v br s), 7.47 (1H, s), 7.30-7.21 (5H, m), 4.12 (2H, s).

Intermediate 3B.
2-(Benzylthio)-6-(trifluoromethyl)pyridine

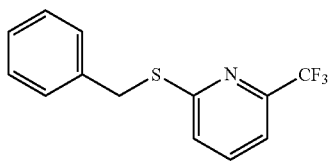 [SMILES: FC(F)(F)c1cccc(SCc2ccccc2)n1]

To a suspension of sodium hydride (0.170 g, 4.24 mmol) in tetrahydrofuran (10 ml) was added benzylthiol (0.338 ml, 2.88 mmol) dropwise at 0° C. The reaction mixture was stirred at 0° C. for 15 minutes then 2-fluoro-6-(trifluoromethyl)pyridine (0.365 ml, 3.03 mmol) was added dropwise. The reaction mixture was stirred at 0° C. for 30 minutes. Methanol (1 ml) was added carefully and the reaction mixture was stirred at 0° C. for a further 10 minutes then water (5 ml) and dichloromethane (10 ml) were added. The organic layer was recovered using a phase separator cartridge then concentrated in vacuo to give 2-(benzylthio)-6-(trifluoromethyl)pyridine (538 mg) as a colourless oil. LCMS: RT 2.80 min, m+H=270.1.

Intermediate 4A.
4-(Benzylthio)-2-methyl-2H-1,2,3-triazole

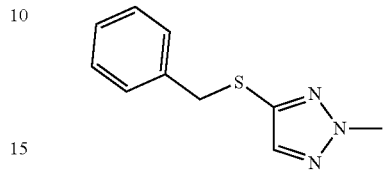

Iodomethane (2.409 ml, 38.7 mmol) was added dropwise to a mixture of 4-(benzylthio)-1H-1,2,3-triazole (3.7 g, 19.35 mmol) and potassium carbonate (5.88 g, 42.6 mmol) in N,N-dimethylformamide (40 ml) at 0° C. The reaction mixture was then allowed to warm to room temperature and stirred for 1 hour. Water (40 ml) and ethyl acetate (40 ml) were added and the phases separated. The organic phase was washed with water (2×40 ml), brine (40 ml), dried (sodium sulfate) and solvent was removed to give a yellow oil. The crude product was purified by column chromatography on silica gel (gradient: 0-100% ethyl acetate in isohexane) to afford 4-(benzylthio)-2-methyl-2H-1,2,3-triazole (1.61 g) as the major and first-eluting regioisomeric product, as a colourless oil, LCMS: RT 2.05 min, m+H=206; 1H NMR (400 MHz, DMSO-d6): δ 7.68 (1H, s), 7.35-7.19 (5H, m), 4.18 (2H, s), 4.11 (3H, s).

Intermediate 4B.
4-(Benzylthio)-1-methyl-1H-1,2,3-triazole

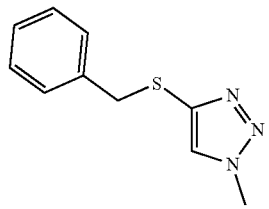

Obtained as a pale yellow oil (883 mg) as the third-eluting regioisomeric product from the reaction above. LCMS: RT 1.68 min, m+H=206; 1H NMR (400 MHz, DMSO-d6): δ 8.02 (1H, s), 7.34-7.19 (5H, m), 4.12 (2H, s), 4.00 (3H, s).

The following intermediates were similarly prepared from appropriate starting materials:

Intermediate 4C.
4-(Benzylthio)-2-propyl-2H-1,2,3-triazole

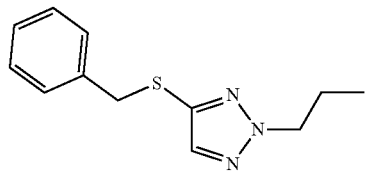 [SMILES: CCCn1ncc(SCc2ccccc2)n1]

Obtained as the major, first-eluting regioisomeric product. LCMS: RT 2.36 min, m+H=234.2; 1H NMR (400 MHz, DMSO-d6): δ 7.69 (1H, s), 7.28-7.27 (4H, m), 7.25-7.20 (1H, m), 4.32 (2H, t, J=7.0 Hz), 4.18 (2H, s), 1.83 (2H, sext, J=7.0 Hz), 0.78 (3H, t, J=7.0 Hz).

Intermediate 4D.
4-(Benzylthio)-2-isopropyl-2H-1,2,3-triazole

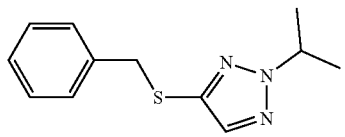 [SMILES: CC(C)n1ncc(SCc2ccccc2)n1]

Obtained as the major, first-eluting regioisomeric product. LCMS: RT 2.41 min, m+H=234; 1H NMR (400 MHz, DMSO-d6): δ 7.67 (1H, s), 7.31-7.21 (5H, m), 4.76 (1H, sept, J=6.7 Hz), 4.17 (2H, s), 1.44 (6H, d, J=6.7 Hz).

Intermediate 4E.
4-(Benzylthio)-2-ethyl-2H-1,2,3-triazole

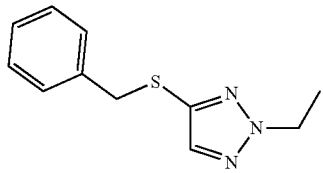

Obtained as the major, first-eluting regioisomeric product. LCMS: RT 2.24 min, m+H=220; 1H NMR (400 MHz, DMSO-d6): δ 7.69 (1H, s), 7.32-7.21 (5H, m), 4.39 (2H, q, J=7.3 Hz), 4.18 (2H, s), 1.40 (3H, t, J=7.3 Hz).

Intermediate 4F.
4-(Benzylthio)-1-methyl-1H-1,2,3-triazole

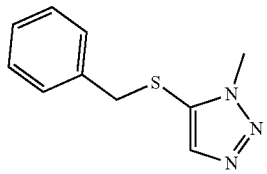

Obtained as a minor, second-eluting regioisomeric product. LCMS: RT 1.79 min, m+H=206; 1H NMR (400 MHz, DMSO-d6): δ 7.71 (1H, s), 7.36-7.23 (3H, m), 7.22-7.14 (2H, m), 4.09 (2H, s), 3.73 (3H, s).

Intermediate 4G.
1-propyl-1H-1,2,3-triazole-5-sulfonyl Chloride

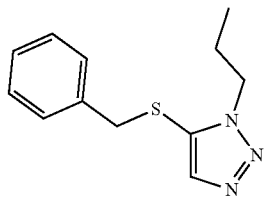 [SMILES: CCCn1nncc1SCc1ccccc1]

Obtained as a minor, second-eluting regioisomeric product. LCMS: RT 2.08 min, m+H=234.2; 1H NMR (400 MHz, DMSO-d6): δ 7.74 (1H, s), 7.38-7.12 (5H, m), 4.13 (2H, s), 4.06 (2H, t, J=7.0 Hz), 1.66 (2H, sext, J=7.0 Hz), 0.74 (3H, t, J=7.0 Hz).

Intermediate 4H.
4-(benzylthio)-1-isopropyl-1H-1,2,3-triazole

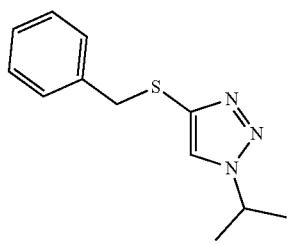 [SMILES: CC(C)n1cc(SCc2ccccc2)nn1]

Obtained as a minor, third-eluting regioisomeric product. LCMS: RT 1.99 min, m+H=234; 1H NMR (400 MHz, DMSO-d6): δ 8.10 (1H, s), 7.30-7.18 (5H, m), 4.76 (1H, sept, J=6.7 Hz), 4.10 (2H, s), 1.43 (6H, d, J=6.7 Hz).

Intermediate 5A.
2-Methyl-2H-1,2,3-triazole-4-sulfonyl Chloride

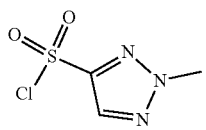

N-chlorosuccinimide (3.38 g, 25.3 mmol) was added to a solution of 4-(benzylthio)-2-methyl-2H-1,2,3-triazole (1.3 g, 6.33 mmol) in acetic acid (32 ml) and water (16 ml) and the resultant mixture was stirred at room temperature for 1 hour. Water (40 ml) was added and the mixture was extracted with ethyl acetate (40 ml). The organic phase was washed with saturated aqueous sodium hydrogen carbonate solution (40 ml), brine (40 ml), dried (magnesium sulfate), and the solvent removed to give 2-methyl-2H-1,2,3-triazole-4-sulfonyl chloride (1.35 g) as a pale yellow oil. LCMS (quenching into morpholine): RT 1.09 min, m+H+morpholine-Cl=233.1; 1H NMR (400 MHz, CDCl3): δ 8.11 (1H, s), 4.36 (3H, s).

The following intermediates were similarly prepared from appropriate starting materials:

Intermediate 5B.
1-Methyl-1H-1,2,3-triazole-4-sulfonyl Chloride

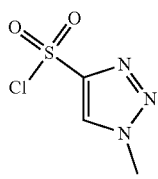

LCMS (quenching into morpholine): RT 0.86 min, m+H+morpholine-Cl=233.1; 1H NMR (400 MHz, CDCl$_3$): δ 8.22 (1H, s), 4.25 (3H, s).

Intermediate 5C.
2-Propyl-2H-1,2,3-triazole-4-sulfonyl Chloride

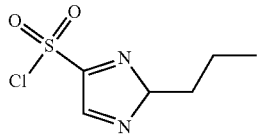

LCMS (quenching into morpholine): RT 1.62 min, m+H+morpholine-Cl=261.2; 1H NMR (400 MHz, CDCl3): δ 8.11 (1H, s), 4.53 (2H, t, J=7.1 Hz), 2.08 (2H, sext, J=7.1 Hz), 0.98 (3H, t, J=7.1 Hz).

Intermediate 5D.
2-Isopropyl-2H-1,2,3-triazole-4-sulfonyl Chloride

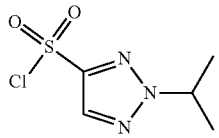

LCMS (quenching into morpholine): RT 1.64 min, m+H+morpholine-Cl=261; 1H NMR (400 MHz, CDCl$_3$): δ 7.62 (1H, s), 4.76 (1H, sept., J=6.7 Hz), 1.46 (6H, d, J=6.7 Hz).

Intermediate 5E.
2-Ethyl-2H-1,2,3-triazole-4-sulfonyl Chloride

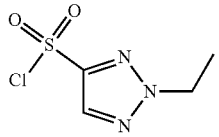

LCMS (quenching into morpholine): RT 1.37 min, m+H+morpholine-Cl=247; 1H NMR (400 MHz, CDCl$_3$): δ 8.11 (1H, s), 4.62 (2H, q, J=7.4 Hz), 1.66 (3H, t, J=7.4 Hz).

Intermediate 5F.
6-(Trifluoromethyl)pyridine-2-sulfonyl Chloride

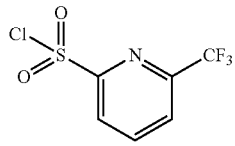 [SMILES: O=S(=O)(Cl)c1cccc(C(F)(F)F)n1]

LCMS (quenching into morpholine): RT 1.84 min, m+H+morpholine-Cl=297.1.

Intermediate 5G.
1-methyl-1H-1,2,3-triazole-5-sulfonyl Chloride

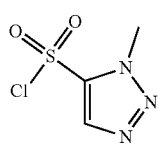

Chlorine gas was bubbled through a solution of 4-(benzylthio)-1-methyl-1H-1,2,3-triazole (200 mg, 0.974 mmol) in dichloromethane (15 ml) and water (3 ml) for 2 minutes at 0° C. then the reaction mixture was stirred at 0° C. for a further 5 minutes. Water (10 ml) was added and the mixture was extracted with dichloromethane (10 ml). The organic phase was dried over magnesium sulfate, filtered and concentrated in vacuo to give 1-methyl-1H-1,2,3-triazole-5-sulfonyl chloride (317 mg) as a colourless oil. LCMS (quenching into morpholine): RT 1.17 min, m+H+morpholine-Cl=233.1; 1H NMR (400 MHz, CDCl$_3$): δ 8.27 (1H, s), 4.40 (3H, s).

The following intermediates was similarly prepared from appropriate starting materials:

Intermediate 5H.
1-propyl-1H-1,2,3-triazole-5-sulfonyl Chloride

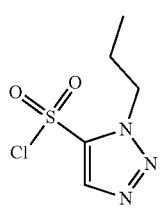

LCMS (quenching into morpholine): RT 1.58 min, m+H+morpholine-Cl=261.1; 1H NMR (400 MHz, CDCl$_3$): δ 8.27 (1H, s), 4.68-4.64 (2H, m), 2.12 (2H, sext, J=7.1 Hz), 1.05 (3H, t, J=7.1 Hz).

Intermediate 5I.
3-fluoro-4-(trifluoromethyl)benzene-1-sulfonyl Chloride

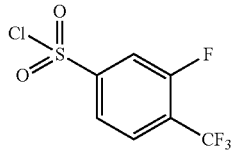

3-Fluoro-4-(trifluoromethyl)aniline (5 g, 27.9 mmol) was dissolved in acetonitrile (10 ml), cooled to 0° C., and treated with tetrafluoroboric acid (48% aqueous solution, 6.49 ml, 41.9 mmol) and tert-butyl nitrite (4.98 ml, 41.9 mmol). The reaction mixture was maintained at 0° C. for 1 hour. In the meantime, a suspension of copper (I) chloride (4.15 g, 41.9 mmol) in acetonitrile (40 ml) at 0° C. was saturated with sulfur dioxide gas by bubbling the gas through the suspension with vigorous stirring for 30 minutes. When the diazotization reaction was complete after 1 hour, this solution was added dropwise to the suspension of copper (I) chloride, causing vigorous evolution of gas. The reaction mixture was then allowed to warm to room temperature and stirred for 1 hour, after which time it was poured onto 100 ml of an ice/water slurry. Diethyl ether (150 ml) was added, causing a precipitate to form, which was removed by filtration. The filtrate was washed with water (100 ml) and brine (100 ml), dried over magnesium sulfate, filtered, and concentrated in vacuo to give 3-fluoro-4-(trifluoromethyl)benzene-1-sulfonyl chloride (6.62 g) as an orange oil. LCMS (quenching into morpholine): RT 2.25 min, m+H+morpholine-Cl=314.1.

Intermediate 5J.
1-isopropyl-1H-1,2,3-triazole-4-sulfonyl Chloride

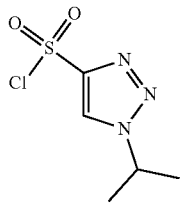

N-chlorosuccinimide (0.458 g, 3.43 mmol) was added to a solution of 4-(benzylthio)-1-isopropyl-1H-1,2,3-triazole (0.20 g, 0.857 mmol) in acetic acid (6 ml) and water (3 ml) and the resultant mixture was stirred at room temperature for 1 hour. Water (8 ml) was added and the mixture was extracted with ethyl acetate (8 ml). The organic phase was washed with saturated aqueous sodium hydrogen carbonate solution (8 ml), brine (8 ml), dried (magnesium sulfate), and the solvent removed to give 1-isopropyl-1H-1,2,3-triazole-4-sulfonyl chloride (311 mg) as a colourless oil. LCMS (quenching into morpholine): RT 1.47 min, m+H+morpholine-Cl=261; 1H NMR (400 MHz, CDCl$_3$): δ 8.26 (1H, s), 4.95 (1H, sept., J=6.7 Hz), 1.68 (6H, d, J=6.7 Hz).

The following intermediates was similarly prepared from appropriate starting materials:

Intermediate 5K. 2H-1,2,3-triazole-4-sulfonyl Chloride

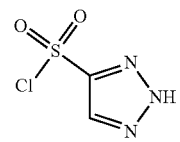

LCMS (quenching into morpholine): RT 1.64 min, m+H+morpholine-Cl=219.1; 1H NMR (400 MHz, CDCl$_3$): δ 9.06 (1H, br s), 8.31 (1H, s).

Intermediate 6A. (R)-tert-butyl 1-(4-fluorophenyl)-4a-(thiazole-4-carbonyl)-4a,5,7,8-tetrahydro-1H-pyrazolo[3,4-g]isoquinoline-6(4H)-carboxylate

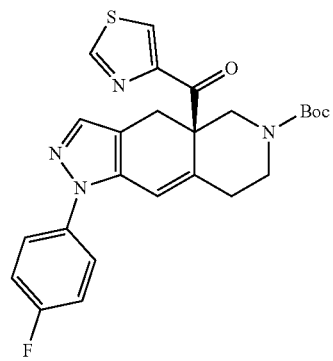

A solution of 4-bromo-2-(trimethylsilyl)thiazole (3.00 g, 12.70 mmol) in dry ether (3 mL) was added to a solution of isopropylmagnesium chloride 2M in tetrahydrofuran (6.35 ml, 12.70 mmol) in dry ether (16 mL) at 0° C. The resulting suspension was stirred at 0° C. for 50 minutes. A solution of (R)-6-tert-butyl 4a-methyl 1-(4-fluorophenyl)-4a,5,7,8-tetrahydro-1H-pyrazolo[3,4-g]isoquinoline-4a,6(4H)-dicarboxylate (1.81 g, 4.23 mmol) in dry ether:tetrahydrofuran (4:1; total volume 15 mL) was added dropwise to the suspension at 0° C., and the reaction mixture was stirred for 3.5 hours at room temperature. Water (50 mL) was added and the reaction mixture was stirred at room temperature for 10 minutes. The aqueous layer was extracted with ethyl acetate (3×50 mL). The combined organic extracts were washed with brine (50 mL), dried over magnesium sulfate, filtered and concentrated in vacuo to give an orange oil. The crude orange oil was diluted with acetonitrile (30 mL) and 1 M HCl (4.2 mL), and stirred at room temperature for 45 minutes. The reaction was diluted with ethyl acetate (100 mL) and washed sequentially with brine (50 mL), saturated aqueous sodiumhydrogen carbonate solution (50 mL) then brine (50 mL). The organic layer was dried over magnesium sulfate and concentrated in vacuo to give an orange oil. The crude product was purified by column chromatography on silica gel (gradient: 0-45% ethyl acetate in isohexane) to afford (R)-tert-butyl 1-(4-fluorophenyl)-4a-(thiazole-4-carbonyl)-4a,5,7,8-tetrahydro-1H-pyrazolo[3,4-g]isoquinoline- 6(4H)-carboxylate as a pale yellow foamy solid (932 mg). LCMS (Method F, ES-API): RT 2.55 min, m+H=481.0.

Intermediate 7A. (4aR,8aS)-tert-butyl 1-(4-fluorophenyl)-4a-(thiazole-4-carbonyl)-4a,5,7,8,8a,9-hexahydro-1H-pyrazolo[3,4-g]isoquinoline-6(4H)-carboxylate

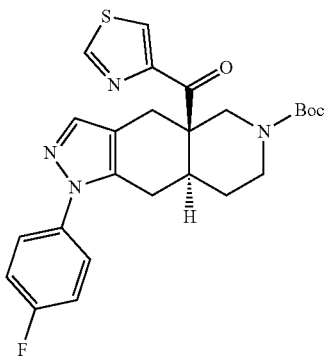

A solution of (R)-tert-butyl 1-(4-fluorophenyl)-4a-(thiazole-4-carbonyl)-4a,5,7,8-tetrahydro-1H-pyrazolo[3,4-g]isoquinoline-6(4H)-carboxylate (420 mg, 0.874 mmol) in methanol (40 mL) was hydrogenated in the H-Cube (10% Palladium/Carbon, 30×4 mm, Full hydrogen, 55° C., 1 mL/min). The solvent was removed to give (4aR,8aS)-tert-butyl 1-(4-fluorophenyl)-4a-(thiazole-4-carbonyl)-4a,5,7,8,8a,9-hexahydro-1H-pyrazolo[3,4-g]isoquinoline-6(4H)-carboxylate as an orange solid (385 mg). LCMS (Method F, ES-API): RT 2.51 min, m+H=483.2.

Example 1A. ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone

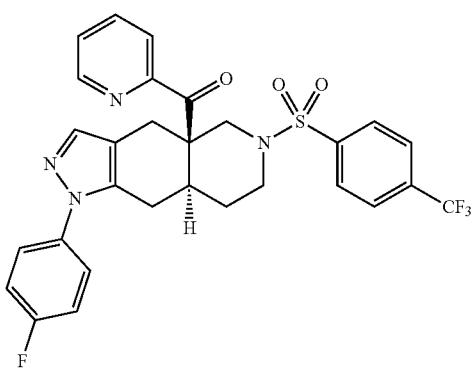 [SMILES: O=C(c1ccccn1)[C@]12Cc3cnn(-c4ccc(F)cc4)c3C[C@@H]1CCN(S(=O)(=O)c1ccc(C(F)(F)F)cc1)C2]

A solution of 2-bromopyridine (0.109 ml, 1.116 mmol) in dry tetrahydrofuran (2 ml) was added to a solution of butyllithium (2.5M in hexanes) (0.417 ml, 1.042 mmol) in dry tetrahydrofuran (1.2 ml), and the reaction mixture stirred at −78° C. under nitrogen for 45 minutes. A solution of (4aR,8aS)-methyl 1-(4-fluorophenyl)-6-((4-(trifluoromethyl)phenyl)sulfonyl)-4,4a,5,6,7,8,8a,9-octahydro-1H-pyrazolo[3,4-g]isoquinoline-4a-carboxylate (0.2 g, 0.372 mmol) in dry tetrahydrofuran (2 ml) was then added dropwise. The reaction mixture was stirred at −78° C. for 45 minutes, then quenched by the addition of 10:1 methanol: acetic acid (5 ml), and stirred at room temperature for an additional 10 minutes. The mixture was diluted with ethyl acetate (200 ml), washed with saturated aqueous ammonium chloride solution (2×50 ml) and brine (50 ml), dried (magnesium sulfate), filtered and evaporated to give a colourless gum. The crude product was purified by column chromatography on silica gel (eluent: 10% ethyl acetate in dichloromethane) to afford ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone (0.06 g) as a white solid, LCMS: RT 2.76 min, m+H=585.0; 1H NMR (400 MHz, CDCl$_3$): δ 8.60-8.56 (1H, m), 7.81-7.76 (4H, m), 7.70-7.65 (2H, m), 7.48-7.39 (3H, m), 7.29 (1H, s), 7.16-7.10 (2H, m), 5.62 (1H, dd, J=12.3, 2.0 Hz), 4.27 (1H, d, J=16.2 Hz), 3.99-3.94 (1H, m), 3.40 (1H, dd, J=16.7, 11.2 Hz), 2.69 (1H, dd, J=16.4, 5.9 Hz), 2.56-2.40 (4H, m), 1.79-1.68 (2H, m).

The following examples were similarly prepared from the appropriate intermediate:

Example 1B. ((4aR,8aS)-6-((3,4-dichlorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone

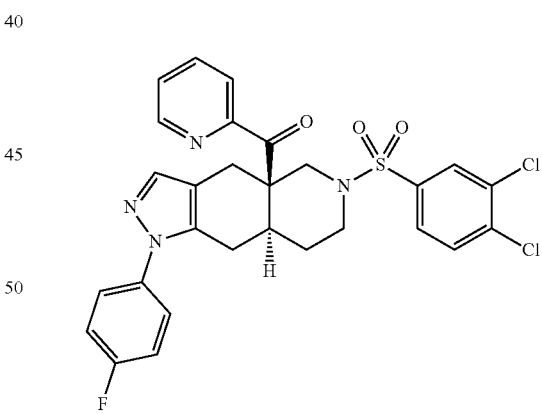

LCMS: RT 3.34 min, m+H=584.8/586.8; 1H NMR (400 MHz, CDCl$_3$): δ 8.56 (1H, dt, J=4.8, 1.3 Hz), 7.79-7.78 (2H, m), 7.72 (1H, d, J=1.9 Hz), 7.50-7.41 (5H, m), 7.29 (1H, s), 7.17-7.11 (2H, m), 5.56 (1H, dd, J=12.3, 1.9 Hz), 4.26 (1H, d, J=16.9 Hz), 3.98-3.94 (1H, m), 3.39 (1H, dd, J=16.0, 11.8 Hz), 2.69 (1H, dd, J=16.1, 6.0 Hz), 2.58-2.40 (4H, m), 1.81-1.70 (2H, m).

Example 1C. ((4aR,8aS)-6-((3,4-difluorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone

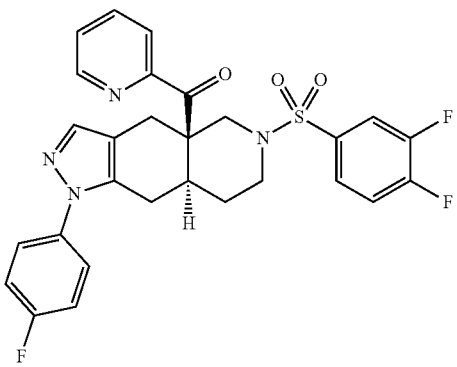 [SMILES: O=C(c1ccccn1)[C@]12Cc3cnn(-c4ccc(F)cc4)c3C[C@@H]1CCN(S(=O)(=O)c1ccc(F)c(F)c1)C2]

LCMS: RT 2.63 min, m+H=553.0; 1H NMR (400 MHz, CDCl$_3$): δ 8.60-8.59 (1H, m), 7.83-7.77 (2H, m), 7.50-7.40 (5H, m), 7.30 (1H, s), 7.25-7.18 (1H, m), 7.17-7.11 (2H, m), 5.57 (1H, dd, J=12.3, 2.0 Hz), 4.29 (1H, d, J=16.9 Hz), 3.95-3.92 (1H, m), 3.40 (1H, dd, J=16.0, 11.8 Hz), 2.69 (1H, dd, J=16.3, 6.0 Hz), 2.56-2.40 (4H, m), 1.80-1.68 (2H, m).

Example 2A. ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone

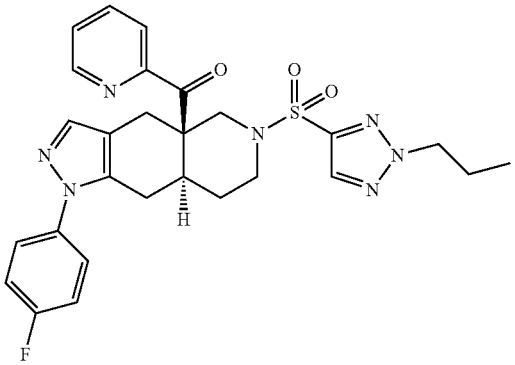 [SMILES: CCCn1ncc(S(=O)(=O)N2CC[C@H]3Cc4c(cnn4-c4ccc(F)cc4)C[C@]3(C(=O)c3ccccn3)C2)n1]

A solution of (4aR,8aS)-tert-butyl 1-(4-fluorophenyl)-4a-picolinoyl-4a,5,7,8,8a,9-hexahydro-1H-pyrazolo[3,4-g]isoquinoline-6(4H)-carboxylate (200 mg, 0.420 mmol) in 4M HCl/dioxane (2098 μl, 8.39 mmol) was stirred at room temperature for 45 minutes. The solvent was removed to give a pale yellow solid, which was dissolved in dichloromethane (8 mL) and diisopropylamine (367 μl, 2.098 mmol) and then 2-propyl-2H-1,2,3-triazole-4-sulfonyl chloride (117 mg, 0.420 mmol) was added. The reaction mixture was stirred at room temperature for 15 minutes, then the solvent was removed to give a brown oil. The crude product was purified by column chromatography on silica gel (gradient: 0-70% ethyl acetate in cyclohexane) to afford ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone (156 mg) as a white solid, LCMS: RT 2.60 min, m+H=550.0; 1H NMR (400 MHz, CDCl$_3$): δ 8.66 (1H, ddd, J=4.7, 1.7, 0.9 Hz), 7.85-7.76 (3H, m), 7.51-7.45 (2H, m), 7.43 (1H, ddd, J=7.1, 4.7, 1.7 Hz), 7.33 (1H, s), 7.19-7.09 (2H, m), 5.68 (1H, dd, J=12.4, 2.1 Hz), 4.43 (2H, t, J=7.1 Hz), 4.37 (1H, d, J=16.2 Hz), 4.00-3.93 (1H, m), 3.46 (1H, dd, J=16.2, 11.1 Hz), 2.70 (1H, dd, J=16.2, 6.0 Hz), 2.64-2.36 (4H, m), 2.02 (2H, sextet, J=7.3 Hz), 1.79-1.71 (2H, m), 0.94 (3H, t, J=7.3 Hz).

The following examples were similarly prepared from the appropriate intermediate:

Example 2B. ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone

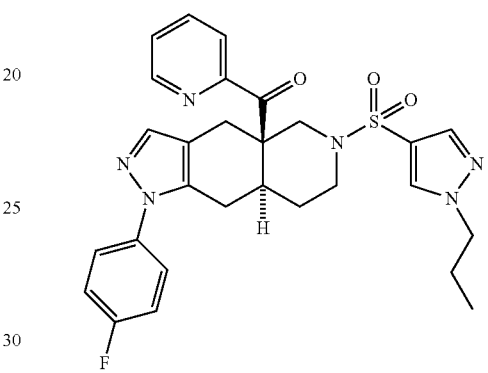

LCMS: RT 2.45 min, m+H=549.1; 1H NMR (400 MHz, CDCl$_3$): δ 8.64 (1H, ddd, J=4.7, 1.7, 0.9 Hz), 7.85-7.82 (1H, m), 7.79 (1H, td, J=7.3, 1.7 Hz), 7.70-7.64 (2H, m), 7.52-7.45 (2H, m), 7.43 (1H, ddd, J=7.3, 4.8, 1.5 Hz), 7.33 (1H, s), 7.19-7.08 (2H, m), 5.52 (1H, dd, J=11.9, 2.1 Hz), 4.35 (1H, d, J=16.2 Hz), 4.15-4.02 (2H, m), 3.88-3.81 (1H, m), 3.45 (1H, dd, J=15.5, 11.1 Hz), 2.69 (1H, dd, J=16.2, 6.0 Hz), 2.56 (1H, d, J=16.2 Hz), 2.48-2.33 (2H, m), 2.26 (1H, d, J=11.9 Hz), 1.90 (2H, sextet, J=7.3 Hz), 1.82-1.65 (2H, m), 0.91 (3H, t, J=7.3 Hz).

Example 2C. ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

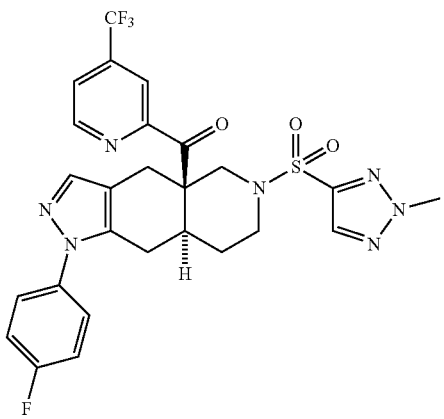 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

LCMS: RT 2.61 min, m+H=590.0; 1H NMR (400 MHz, CDCl$_3$): δ 8.86 (1H, d, J=5.0 Hz), 8.10 (1H, s), 7.81 (1H, s), 7.70-7.62 (1H, m), 7.52-7.44 (2H, m), 7.33 (1H, s), 7.20-7.11 (2H, m), 5.64 (1H, dd, J=12.5, 2.0 Hz), 4.26 (3H, s), 4.25 (1H, d, J=16.2 Hz), 4.02-3.90 (1H, m), 3.44 (1H, dd, J=16.2, 10.8 Hz), 2.73 (1H, dd, J=16.2, 5.9 Hz), 2.67-2.53 (3H, m), 2.43 (1H, qd, J=13.2, 5.0 Hz), 1.88-1.75 (2H, m).

Example 2D. ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

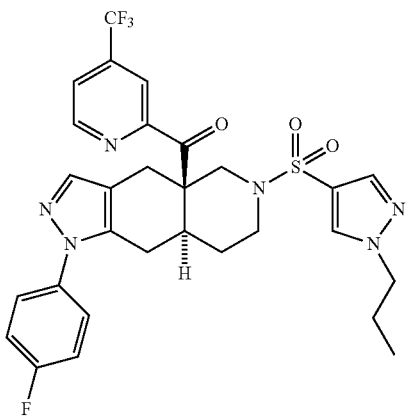 [SMILES: CCCn1cc(S(=O)(=O)N2CC[C@H]3Cc4c(cnn4-c4ccc(F)cc4)C[C@]3(C(=O)c3cc(C(F)(F)F)ccn3)C2)cn1]

LCMS: RT 2.72 min, m+H=617.0; 1H NMR (400 MHz, CDCl$_3$): δ 8.86 (1H, d, J=5.0 Hz), 8.13-8.08 (1H, m), 7.70-7.62 (3H, m), 7.51-7.42 (2H, m), 7.33 (1H, s), 7.20-7.10 (2H, m), 5.49 (1H, dd, J=12.0, 2.0 Hz), 4.23 (1H, d, J=16.1 Hz), 4.09 (2H, t, J=7.2 Hz), 3.88-3.78 (1H, m), 3.43 (1H, dd, J=16.1, 11.0 Hz), 2.71 (1H, dd, J=16.3, 6.0 Hz), 2.60 (1H, d, J=16.3 Hz), 2.49-2.32 (2H, m), 2.27 (1H, d, J=12.1 Hz), 1.90 (2H, sextet, J=7.2 Hz), 1.83-1.68 (2H, m), 0.91 (3H, t, J=7.2 Hz).

Example 2E. ((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(thiazol-2-yl)methanone

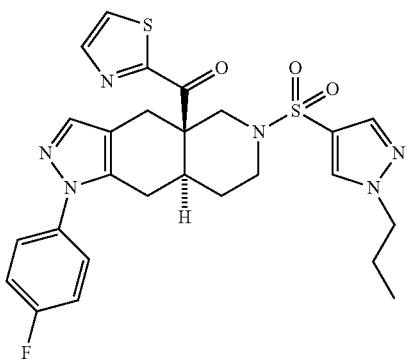 [SMILES: CCCn1cc(S(=O)(=O)N2CC[C@H]3Cc4c(cnn4-c4ccc(F)cc4)C[C@]3(C(=O)c3nccs3)C2)cn1]

LCMS: RT 2.45 min, m+H=554.9; 1H NMR (400 MHz, CDCl$_3$): δ 8.04 (1H, d, J=3.1 Hz), 7.74 (1H, s), 7.69 (1H, d, J=0.5 Hz), 7.65 (1H, d, J=3.1 Hz), 7.53-7.46 (2H, m), 7.40 (1H, s), 7.21-7.13 (2H, m), 5.47 (1H, dd, J=12.0, 2.1 Hz), 4.23 (1H, d, J=16.2 Hz), 4.12 (2H, t, J=7.2 Hz), 3.94-3.85 (1H, m), 3.44 (1H, dd, J=16.2, 11.1 Hz), 2.72 (1H, dd, J=16.2, 6.0 Hz), 2.62 (1H, d, J=16.2 Hz), 2.54-2.41 (2H, m), 2.36 (1H, d, J=12.1 Hz), 1.95 (2H, sextet, J=7.3 Hz), 1.87-1.75 (2H, m), 0.95 (3H, t, J=7.3 Hz).

Example 2F. ((4aR,8aS)-1-(4-fluorophenyl)-6-((3-fluorophenyl)sulfonyl)-4,4a,5,6,7,8,8a,9-octahydro-1H-pyrazolo[3,4-g]isoquinolin-4a-yl)(pyridin-2-yl)methanone

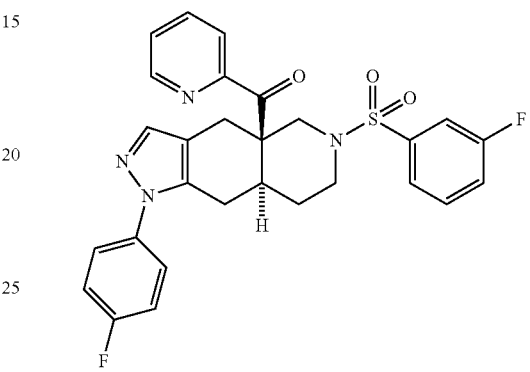

LCMS: RT 2.65 min, m+H=534.9; 1H NMR (400 MHz, CDCl$_3$): δ 8.66 (1H, ddd, J=4.7, 1.7, 1.0 Hz), 7.88-7.77 (2H, m), 7.53-7.43 (5H, m), 7.41-7.35 (1H, m), 7.35 (1H, s), 7.29-7.22 (1H, m), 7.22-7.12 (2H, m), 5.62 (1H, dd, J=12.2, 2.1 Hz), 4.35 (1H, d, J=16.2 Hz), 3.98-3.86 (1H, m), 3.44 (1H, dd, J=16.2, 11.1 Hz), 2.70 (1H, dd, J=16.2, 5.9 Hz), 2.56 (1H, d, J=16.2 Hz), 2.51-2.41 (2H, m), 2.39 (1H, d, J=12.2 Hz), 1.83-1.65 (2H, m).

Example 2G. ((4aR,8aS)-1-(4-fluorophenyl)-6-((3-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone

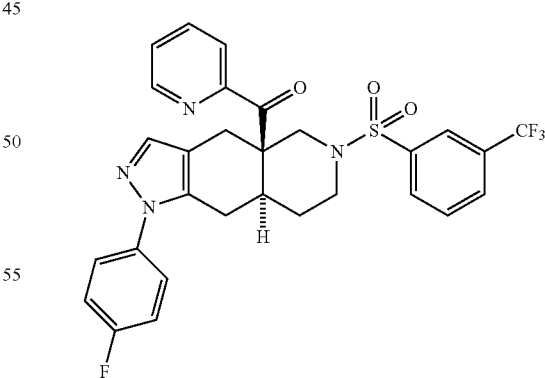

LCMS: RT 2.79 min, m+H=584.9; 1H NMR (400 MHz, CDCl$_3$): δ 8.66-8.61 (1H, m), 7.94 (1H, s), 7.88 (1H, br. d, J=7.9 Hz), 7.84-7.77 (3H, m), 7.61 (1H, t, J=7.8 Hz), 7.53-7.41 (3H, m), 7.33 (1H, s), 7.21-7.11 (2H, m), 5.66 (1H, dd, J=12.2, 2.1 Hz), 4.31 (1H, d, J=16.2 Hz), 4.03-3.91 (1H, m), 3.43 (1H, dd, J=16.2, 11.2 Hz), 2.71 (1H, dd, J=16.2, 5.9 Hz), 2.62-2.35 (4H, m), 1.85-1.68 (2H, m).

Example 2H. ((4aR,8aS)-1-(4-fluorophenyl)-6-((1-methyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

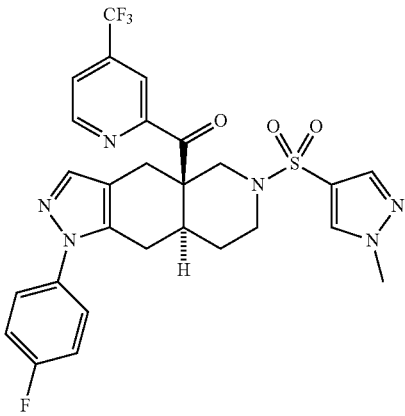 [SMILES: Cn1cc(S(=O)(=O)N2CC[C@H]3Cc4c(cnn4-c4ccc(F)cc4)C[C@]3(C(=O)c3cc(C(F)(F)F)ccn3)C2)cn1]

Using trifluoroacetic acid/dichloromethane in place of HCl/dioxane. LCMS: RT 2.44 min, m+H=589.2; 1H NMR (400 MHz, CDCl$_3$): δ 8.84 (1H, d, J=5.0 Hz), 8.10 (1H, m), 7.66-7.65 (3H, m), 7.50-7.45 (2H, m), 7.33 (1H, s), 7.18-7.12 (2H, m), 5.47 (1H, dd, J=11.8, 2.0 Hz), 4.22 (1H, d, J=16.2 Hz), 3.92 (3H, s), 3.85-3.83 (1H, m), 3.42 (1H, dd, J=16.5, 11.4 Hz), 2.71 (1H, dd, J=16.5, 5.8 Hz), 2.60 (1H, d, J=16.2 Hz), 2.46-2.34 (2H, m), 2.29 (1H, d, J=12.0 Hz), 1.84-1.70 (2H, m).

Example 2I. ((4aR,8aS)-1-(4-fluorophenyl)-6-((1-methyl-1H-pyrazol-3-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

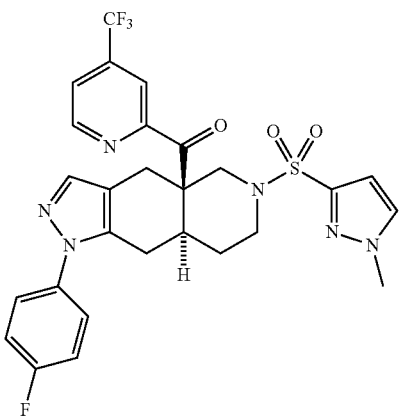 [SMILES: Cn1ccc(S(=O)(=O)N2CC[C@H]3Cc4c(cnn4-c4ccc(F)cc4)C[C@]3(C(=O)c3cc(C(F)(F)F)ccn3)C2)n1]

Using trifluoroacetic acid/dichloromethane in place of HCl/dioxane. LCMS: RT 2.49 min, m+H=589.2; 1H NMR (400 MHz, CDCl$_3$): δ 8.85 (1H, d, J=5.0 Hz), 8.10-8.09 (1H, m), 7.65-7.63 (1H, m), 7.50-7.45 (2H, m), 7.38 (1H, d, J=2.5 Hz), 7.34 (1H, s), 7.18-7.12 (2H, m), 6.55 (1H, d, J=2.5 Hz), 5.57 (1H, dd, J=11.8, 2.0 Hz), 4.27 (1H, d, J=16.2 Hz), 3.97 (3H, s), 3.93-3.89 (1H, m), 3.44 (1H, dd, J=16.2, 10.9 Hz), 2.71 (1H, dd, J=16.4, 6.0 Hz), 2.63-2.55 (2H, m), 2.54 (1H, d, J=12.2 Hz), 2.45-2.34 (1H, m), 1.82-1.74 (2H, m).

Example 2J. ((4aR,8aS)-1-(4-fluorophenyl)-6-((1-methyl-1H-pyrazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone Using trifluoroacetic acid/dichloromethane in place of HCl/dioxane. LCMS: RT 2.60 min, m+H=589.2; 1H NMR (400 MHz, CDCl$_3$): δ 8.77 (1H, d, J=4.9 Hz), 8.07-8.06 (1H, m), 7.66-7.64 (1H, m), 7.49-7.44 (2H, m), 7.30 (1H, d, J=2.0 Hz), 7.29 (1H, s), 7.18-7.12 (2H, m), 6.60 (1H, d, J=2.0 Hz), 5.55 (1H, dd, J=12.6, 2.2 Hz), 4.18 (1H, d, J=16.2 Hz), 4.01-3.97 (1H, m), 3.91 (3H, s), 3.37 (1H, dd, J=16.4, 11.1 Hz), 2.76-2.69 (2H, m), 2.68 (1H, d, J=12.6 Hz), 2.61 (1H, d, J=16.2 Hz), 2.52-2.40 (1H, m), 1.89-1.80 (2H, m).

Example 2K. ((4aR,8aS)-6-((1-ethyl-1H-pyrazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone

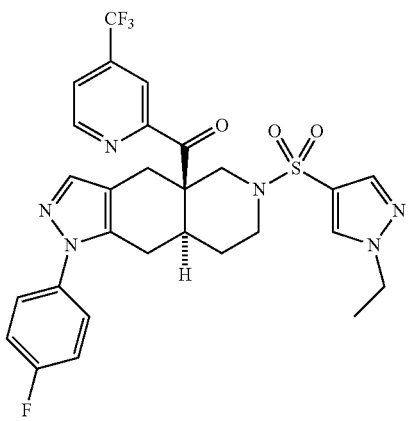 [SMILES: CCn1cc(S(=O)(=O)N2CC[C@H]3Cc4c(cnn4-c4ccc(F)cc4)C[C@]3(C(=O)c3cc(C(F)(F)F)ccn3)C2)cn1]

Using trifluoroacetic acid/dichloromethane in place of HCl/dioxane. LCMS: RT 2.54 min, m+H=603.2; 1H NMR (400 MHz, CDCl$_3$): δ 8.85 (1H, d, J=5.1 Hz), 8.10 (1H, m), 7.70 (1H, s), 7.66-7.65 (2H, m), 7.50-7.45 (2H, m), 7.33 (1H, s), 7.18-7.12 (2H, m), 6.60 (1H, d, J=2.0 Hz), 5.48 (1H, dd, J=12.1, 2.0 Hz), 4.23 (1H, d, J=16.4 Hz), 4.18 (2H, q, J=7.2 Hz), 3.85-3.83 (1H, m), 3.42 (1H, dd, J=16.4, 11.1 Hz), 2.71 (1H, dd, J=16.2, 6.0 Hz), 2.60 (1H, d, J=16.2 Hz), 2.46-2.34 (1H, m), 2.29 (1H, d, J=12.1 Hz), 1.82-1.71 (2H, m), 1.51 (3H, t, J=7.2 Hz).

Example 2L. ((4aR,8aS)-6-((1-ethyl-1H-pyrazol-5-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone

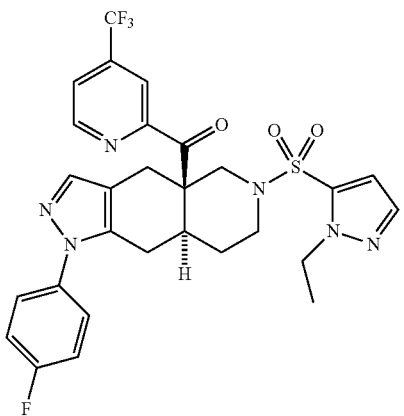 [SMILES: CCn1nccc1S(=O)(=O)N1CC[C@H]2Cc3c(cnn3-c3ccc(F)cc3)C[C@]2(C(=O)c2cc(C(F)(F)F)ccn2)C1]

Using trifluoroacetic acid/dichloromethane in place of HCl/dioxane. LCMS: RT 2.70 min, m+H=603.3; 1H NMR (400 MHz, CDCl$_3$): δ 8.78 (1H, d, J=5.0 Hz), 8.07 (1H, m), 7.66-7.64 (1H, m), 7.49-7.44 (2H, m), 7.36 (1H, d, J=2.0 Hz), 7.29 (1H, s), 7.18-7.12 (2H, m), 6.58 (1H, d, J=2.0 Hz), 5.57 (1H, dd, J=12.5, 2.0 Hz), 4.32 (3H, m),3.98-3.94 (1H, m),3.38 (1H, dd, J=16.2, 10.8 Hz), 2.76-2.69 (2H, m), 2.66 (1H, d, J=12.6 Hz), 2.61 (1H, d, J=16.2 Hz), 2.51-2.40 (1H, m), 1.89-1.80 (2H, m), 1.39 (3H, t, J=7.2 Hz).

Example 2M. ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(thiazol-2-yl)methanone

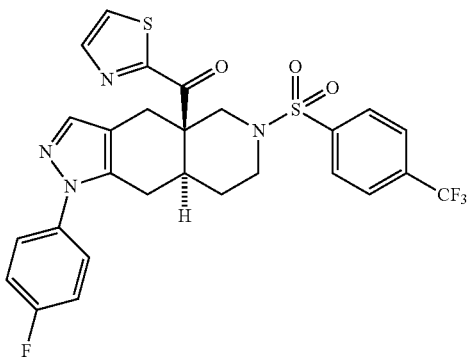 [SMILES: O=C(c1nccs1)[C@]12Cc3cnn(-c4ccc(F)cc4)c3C[C@@H]1CCN(S(=O)(=O)c1ccc(C(F)(F)F)cc1)C2]

LCMS: RT 2.79 min, m+H=590.7; 1H NMR (400 MHz, CDCl$_3$): δ 7.94 (1H, d, J=3.1 Hz), 7.82 (2H, d, J=8.2 Hz), 7.71 (2H, d, J=8.2 Hz), 7.59 (1H, d, J=3.1 Hz), 7.48-7.42 (2H, m), 7.34 (1H, s), 7.17-7.10 (2H, m),5.43 (1H, dd, J=12.3, 2.1 Hz), 4.16 (1H, d, J=16.0 Hz), 4.05-3.96 (1H, m), 3.37 (1H, dd, J=16.0, 10.6 Hz), 2.69 (1H, dd, J=16.4, 5.7 Hz), 2.59-2.42 (4H, m), 1.84-1.77 (2H, m).

Example 2N. ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone

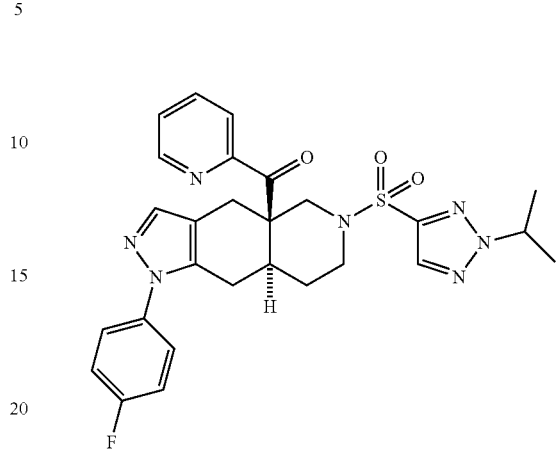

LCMS: RT 2.61 min, m+H=549.9; 1H NMR (400 MHz, CDCl$_3$): δ 8.68 (1H, ddd, J=4.8, 1.7, 1.0 Hz), 7.88-7.78 (3H, m), 7.54-7.42 (3H, m), 7.37 (1H, s), 7.21-7.12 (2H, m), 5.70 (1H, dd, J=12.4, 2.1 Hz), 4.90 (1H, sept, J=6.7 Hz),4.40 (1H, d, J=16.3 Hz), 4.02-3.96 (1H, m), 3.48 (1H, dd, J=16.3, 10.9 Hz), 2.72 (1H, dd, J=16.3, 5.9 Hz), 2.66-2.58 (2H, m), 2.55 (1H, d, J=12.4 Hz), 2.46 (1H, qd, J=13.8, 5.0 Hz),1.83-1.75 (2H, m), 1.62 (6H, d, J=6.7 Hz).

Example 2O. ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone

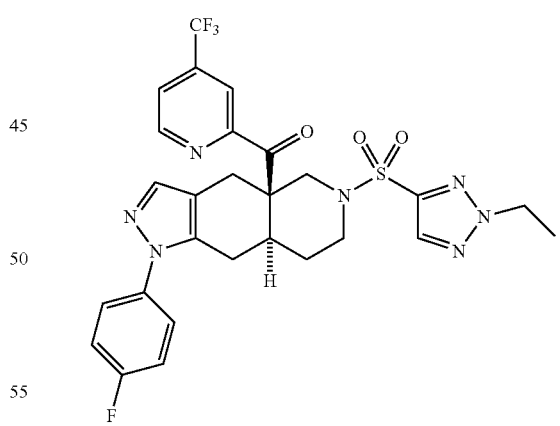

LCMS: RT 2.68 min, m+H=604.3; 1H NMR (400 MHz, CDCl$_3$): δ 8.86 (1H, d, J=5.0 Hz), 8.10 (1H, m), 7.81 (1H, s), 7.67-7.66 (1H, m), 7.50-7.45 (1H, m), 7.33 (1H, s), 7.18-7.12 (2H, m), 5.64 (1H, dd, J=12.4, 2.0 Hz), 4.52 (2H, q, J=7.3 Hz), 4.25 (1H, d, J=16.4 Hz), 3.98-3.93 (1H, m), 3.43 (1H, dd, J=16.4, 11.1 Hz), 2.72 (1H, dd, J=16.2, 5.9 Hz), 2.60 (1H, d, J=16.2 Hz), 2.64-2.58 (2H, m), 2.56 (1H, d, J=12.6 Hz), 2.48-2.36 (1H, m), 1.84-1.76 (2H, m), 1.60 (3H, t, J=7.3 Hz).

Example 2P. ((4aR,8aS)-1-(4-fluorophenyl)-6-((1-methyl-1H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

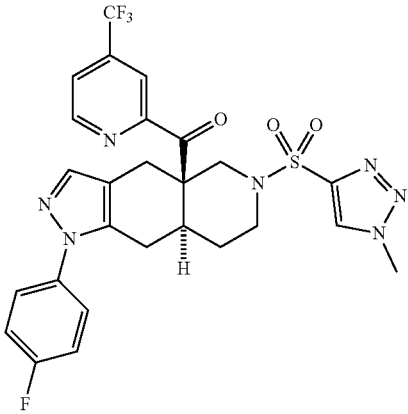 [SMILES: Cn1cc(S(=O)(=O)N2CC[C@H]3Cc4c(cnn4-c4ccc(F)cc4)C[C@]3(C(=O)c3cc(C(F)(F)F)ccn3)C2)nn1]

LCMS: RT 2.45 min, m+H=590.2; 1H NMR (400 MHz, CDCl$_3$): δ 8.85 (1H, d, J=5.0 Hz), 8.11-8.10 (1H, m), 7.88 (1H, s), 7.66-7.65 (1H, m), 7.50-7.45 (2H, m), 7.34 (1H, s), 7.18-7.12 (2H, m), 5.68 (1H, dd, J=12.6, 2.0 Hz), 4.26 (1H, d, J=16.4 Hz), 4.15 (3H, s), 3.97-3.92 (1H, m), 3.43 (1H, dd, J=16.4, 11.1 Hz), 2.78-2.70 (3H, m), 2.63 (1H, d, J=16.2 Hz), 2.47-2.36 (1H, m), 1.87-1.78 (2H, m).

Example 2Q. ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(pyridin-2-yl)methanone

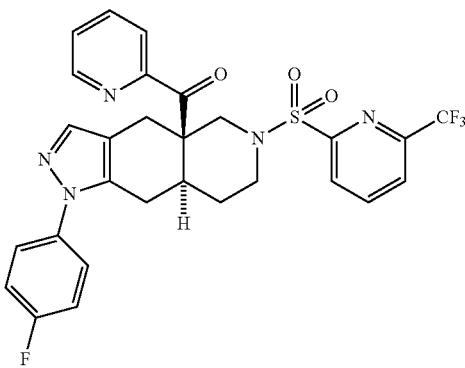

LCMS: RT 2.68 min, m+H=585.6; 1H NMR (400 MHz, CDCl$_3$): δ 8.61-8.53 (1H, m), 7.96 (1H, t, J=7.7 Hz), 7.86 (1H, d, J=7.7 Hz), 7.78-7.68 (3H, m), 7.46-7.39 (2H, m), 7.37 (1H, ddd, J=6.9, 4.8, 2.0 Hz), 7.31 (1H, s), 7.14-7.01 (2H, m), 5.68 (1H, dd, J=12.9, 2.1 Hz), 4.32 (1H, d, J=16.3 Hz), 4.05-3.94 (1H, m), 3.46-3.33 (1H, m), 2.93 (1H, td, J=12.6, 3.1 Hz), 2.91 (1H, d, J=12.9 Hz), 2.65 (1H, dd, J=16.3, 6.0 Hz), 2.54 (1H, d, J=16.3 Hz), 2.37 (1H, qd, J=12.9, 5.1 Hz), 1.87-1.76 (1H, m), 1.76-1.64 (1H, m).

Example 2R. ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-methylpyridin-2-yl)methanone

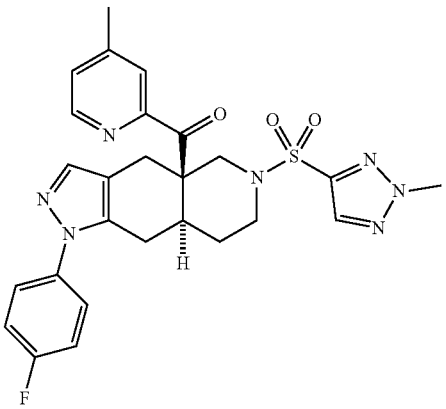 [SMILES: Cc1ccnc(C(=O)[C@]23Cc4cnn(-c5ccc(F)cc5)c4C[C@@H]2CCN(S(=O)(=O)c2cnn(C)n2)C3)c1]

LCMS: RT 2.44 min, m+H=536.3; 1H NMR (400 MHz, CDCl$_3$): δ: 8.49 (1H, d, J=5.0 Hz), 7.80 (1H, s), 7.66-7.65 (1H, m), 7.50-7.45 (2H, m), 7.32 (1H, s), 7.24-7.23 (1H, m), 7.17-7.11 (2H, m), 5.73 (1H, dd, J=12.5, 2.2 Hz), 4.36 (1H, d, J=16.1 Hz), 4.25 (3H, s), 3.98-3.94 (1H, m), 3.44 (1H, dd, J=16.4, 11.3 Hz), 2.69 (1H, dd, J=16.4, 5.9 Hz), 2.64-2.42 (4H, m), 2.37 (3H, s), 1.79-1.70 (2H, m).

Example 2S. ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone

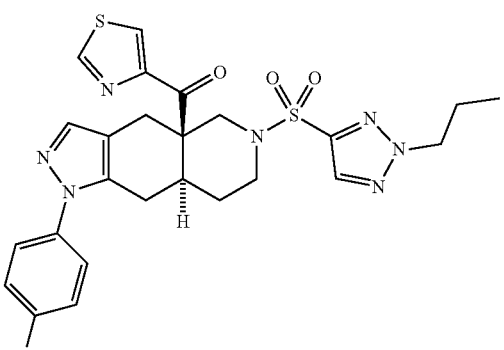

LCMS: RT 2.50 min, m+H=556.2; 1H NMR (400 MHz, CDCl$_3$): δ: 8.85 (1H, d, J=2.2 Hz), 8.18 (1H, d, J=2.2 Hz), 7.83 (1H, s), 7.50-7.44 (2H, m), 7.35 (1H, s), 7.17-7.11 (2H, m), 5.54 (1H, dd, J=12.6, 2.0 Hz), 4.44 (2H, dd, J=7.2 Hz), 4.19 (1H, d, J=16.3 Hz), 3.99-3.95 (1H, m), 3.46 (1H, dd, J=16.4, 11.1 Hz), 2.68 (1H, dd, J=16.4, 5.9 Hz), 2.62-2.48 (4H, m), 2.02 (2H, sext, J=7.2 Hz), 1.83-1.75 (2H, m), 0.94 (3H, t, J=7.2 Hz).

Example 2T. 3-(((4aR,8aS)-1-(4-fluorophenyl)-4a-picolinoyl-4a,5,7,8,8a,9-hexahydro-1H-pyrazolo[3,4-g]isoquinolin-6(4H)-yl)sulfonyl)benzonitrile

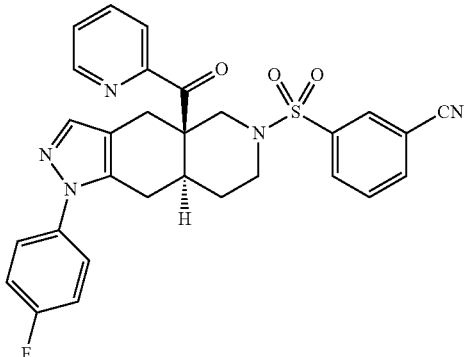

LCMS: RT 2.46 min, m+H=542.2; 1H NMR (400 MHz, CDCl$_3$): δ: 8.63 (1H, ddd, J=4.7, 1.3 Hz), 7.92-7.88 (2H, m), 7.81-7.79 (2H, m), 7.77 (1H, ddd, J=7.7, 1.3 Hz), 7.58 (1H, dt, J=7.7, 0.6 Hz), 7.48-7.42 (3H, m), 7.30 (1H, s), 7.17-7.11 (2H, m), 5.66 (1H, dd, J=12.3, 2.1 Hz), 4.27 (1H, d, J=16.1 Hz), 3.98-3.95 (1H, m), 3.39 (1H, dd, J=16.1, 11.2 Hz), 2.68 (1H, dd, J=16.3, 6.1 Hz), 2.55-2.39 (4H, m), 1.80-1.69 (2H, m).

Example 2U. ((4aR,8aS)-6-((3-fluoro-4-(trifluoromethyl)phenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone

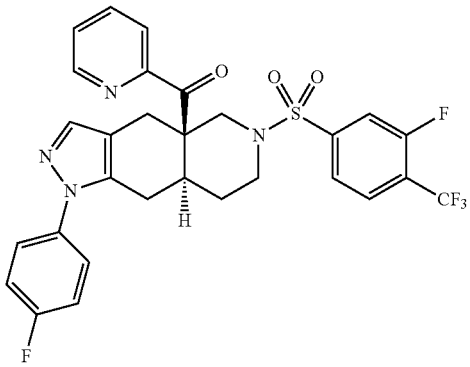 [SMILES: O=C(c1ccccn1)[C@]12Cc3cnn(-c4ccc(F)cc4)c3C[C@@H]1CCN(S(=O)(=O)c1ccc(C(F)(F)F)c(F)c1)C2]

LCMS: RT 2.79 min, m+H=603.3; 1H NMR (400 MHz, CDCl$_3$): δ 8.63 (1H, ddd, J=4.7, 1.3 Hz), 7.79-7.78 (2H, m), 7.66 (1H, dd, J=7.7 Hz), 7.54 (1H, d, J=8.0 Hz), 7.49-7.42 (4H, m), 7.30 (1H, s), 7.17-7.11 (2H, m), 5.64 (1H, dd, J=12.4, 2.0 Hz), 4.26 (1H, d, J=16.1 Hz), 4.00-3.96 (1H, m), 3.39 (1H, dd, J=16.4, 11.2 Hz), 2.69 (1H, dd, J=16.2, 6.0 Hz), 2.60-2.41 (4H, m), 1.80-1.71 (2H, m).

Example 2V. ((4aR,8aS)-1-(4-fluorophenyl)-6-((4-methyl-3,4-dihydro-2H-pyrido[3,2-b][1,4]oxazin-7-yl)sulfonyl)-4,4a,5,6,7,8,8a,9-octahydro-1H-pyrazolo[3,4-g]isoquinolin-4a-yl)(pyridin-2-yl) methanone

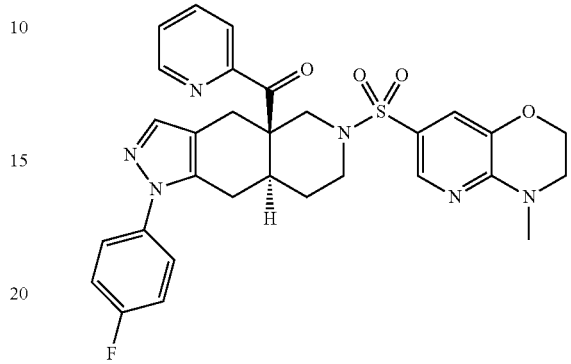

LCMS: RT 2.39 min, m+H=589.3; 1H NMR (400 MHz, CDCl$_3$): δ 8.61 (1H, ddd, J=4.7, 1.6, 0.9 Hz), 8.05 (1H, d, J=2.0 Hz), 7.83-7.81 (1H, m), 7.77 (1H, dd, J=7.4, 1.6 Hz), 7.49-7.44 (2H, m), 7.40 (1H, ddd, J=7.3, 4.7, 1.6 Hz), 7.32 (1H, s), 7.16-7.10 (2H, m), 7.04 (1H, d, J=2.0 Hz), 5.51 (1H, dd, J=12.1, 2.0 Hz), 4.31 (1H, d, J=16.2 Hz), 4.23-4.21 (2H, m), 3.87-3.84 (1H, m), 3.55-3.53 (2H, m), 3.43 (1H, dd, J=16.4, 11.1 Hz), 3.22 (3H, s), 2.67 (1H, dd, J=16.3, 6.1 Hz), 2.54 (1H, d, J=16.2 Hz), 2.47-2.36 (2H, m), 2.32 (1H, J=12.0 Hz), 1.76-1.66 (2H, m).

Example 2W. ((4aR,8aS)-1-(4-fluorophenyl)-6-((1-propyl-1H-1,2,3-triazol-5-yl)sulfonyl)-4,4a,5,6,7,8,8a,9-octahydro-1H-pyrazolo[3,4-g]isoquinolin-4a-yl)(thiazol-2-yl)methanone

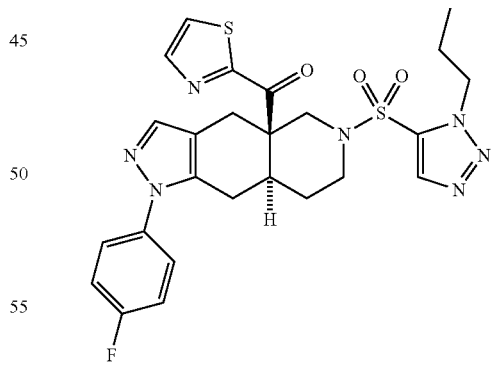

LCMS: RT 2.48 min, m+H=556.2; 1H NMR (400 MHz, CDCl$_3$): δ 7.94 (1H, d, J=3.1 Hz), 7.87 (1H, s), 7.62 (1H, d, J=3.1 Hz), 7.48-7.42 (2H, m), 7.32 (1H, s), 7.17-7.11 (2H, m), 5.45 (1H, dd, J=12.7, 2.1 Hz), 4.38-4.27 (2H, m), 4.14 (1H, d, J=16.1 Hz), 4.06-4.01 (1H, m), 3.37 (1H, dd, J=16.1, 11.1 Hz), 2.86-2.70 (3H, m), 2.61 (1H, d, J=16.1 Hz), 2.53-2.42 (1H, m), 1.97-1.82 (4H, m), 0.94 (3H, t, J=7.3 Hz).

Example 2X. ((4aR,8aS)-1-(4-fluorophenyl)-6-((1-methyl-1H-1,2,3-triazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

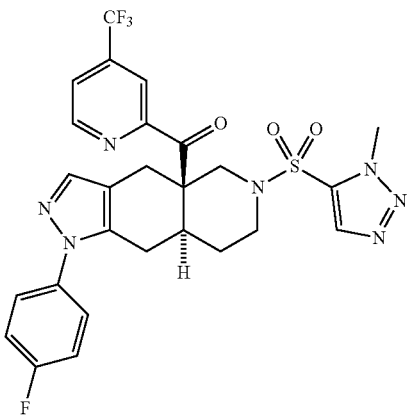 [SMILES: Cn1nncc1S(=O)(=O)N1CC[C@H]2Cc3c(cnn3-c3ccc(F)cc3)C[C@]2(C(=O)c2cc(C(F)(F)F)ccn2)C1]

LCMS: RT 2.56 min, m+H=590.3; 1H NMR (400 MHz, CDCl₃): δ 8.77 (1H, d, J=5.0 Hz), 8.04 (1H, m), 7.89 (1H, s), 7.69-7.67 (1H, m), 7.48-7.43 (2H, m), 7.28 (1H, s), 7.18-7.12 (2H, m), 5.59 (1H, dd, J=12.6, 2.0 Hz), 4.12 (1H, d, J=16.3 Hz), 4.06 (3H, s), 4.06-4.01 (1H, m), 3.35 (1H, dd, J=16.4, 11.2 Hz), 2.82-2.72 (3H, m), 2.61 (1H, d, J=16.2 Hz), 2.47-2.36 (1H, qd, J=13.0, 5.2 Hz), 1.91-1.82 (2H, m).

Example 2Y. ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone

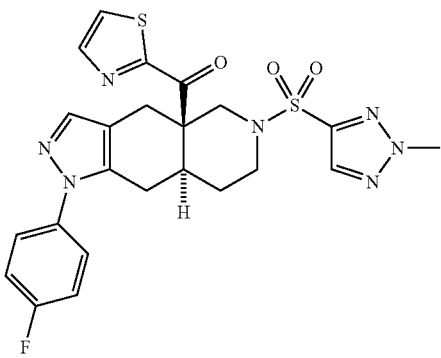 [SMILES: Cn1ncc(S(=O)(=O)N2CC[C@H]3Cc4c(cnn4-c4ccc(F)cc4)C[C@]3(C(=O)c3nccs3)C2)n1]

LCMS: RT 2.30 min, m+H=528.2; 1H NMR (400 MHz, CDCl₃): δ 8.02 (1H, d, J=3.1 Hz), 7.82 (1H, s), 7.61 (1H, d, J=3.1 Hz), 7.49-7.44 (2H, m), 7.35 (1H, s), 7.17-7.10 (2H, m), 5.58 (1H, dd, J=12.6, 2.1 Hz), 4.26 (3H, s), 4.22 (1H, d, J=16.4 Hz), 4.04-3.96 (1H, m), 3.41 (1H, dd, J=16.4, 11.4 Hz), 2.73-2.58 (4H, m), 2.54-2.43 (1H, m), 1.88-1.77 (2H, m).

Example 2Z. ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone

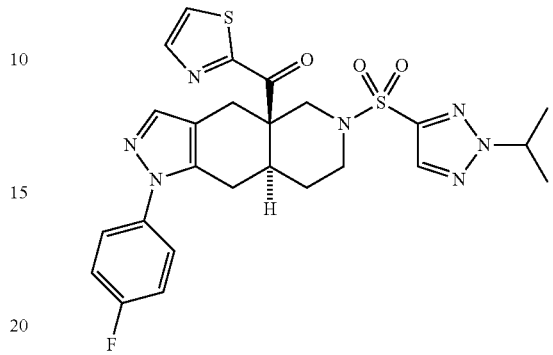

LCMS: RT 2.53 min, m+H=556.2; 1H NMR (400 MHz, CDCl₃): δ 8.03 (1H, d, J=3.1 Hz), 7.80 (1H, s), 7.61 (1H, d, J=3.1 Hz), 7.49-7.44 (2H, m), 7.35 (1H, s), 7.17-7.11 (2H, m), 5.60 (1H, dd, J=12.6, 2.1 Hz), 4.88 (1H, sept, J=6.7 Hz), 4.23 (1H, d, J=16.4 Hz), 4.02-3.98 (1H, m), 3.41 (1H, dd, J=16.1, 11.2 Hz), 2.73-2.58 (4H, m), 2.49 (1H, dq, J=12.5, 5.0 Hz), 1.88-1.74 (2H, m), 1.61 (6H, d, J=6.7 Hz).

Example 2AA. ((4aR,8aS)-1-(4-fluorophenyl)-6-((1-isopropyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone

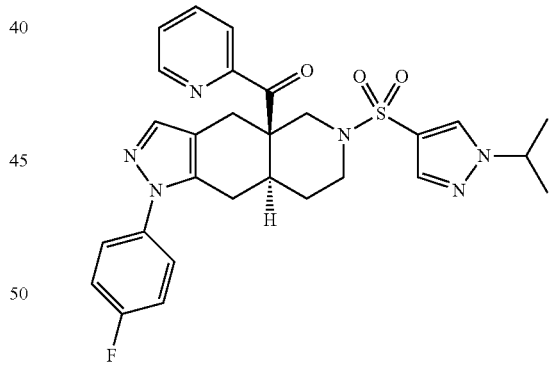

LCMS: RT 2.41 min, m+H=549.3; 1H NMR (400 MHz, CDCl₃): 8.63 (1H, ddd, J=4.7, 1.6, 0.8 Hz), 7.82 (1H, ddd, J=7.8, 1.3, 0.8 Hz), 7.77 (1H, dd, J=7.4, 1.6 Hz), 7.72 (1H, s), 7.64 (1H, d, J=0.8 Hz), 7.49-7.44 (2H, m), 7.41 (1H, ddd, J=7.3, 4.8, 1.6 Hz), 7.31 (1H, s), 7.15-7.09 (2H, m), 5.51 (1H, dd, J=12.0, 2.0 Hz), 4.47 (1H, sept, J=6.7 Hz), 4.34 (1H, d, J=16.1 Hz), 3.85-3.78 (1H, m), 3.43 (1H, dd, J=16.4, 11.2 Hz), 2.68 (1H, dd, J=16.2, 6.0 Hz), 2.56 (1H, d, J=16.2 Hz), 2.46-2.32 (2H, m), 2.26 (1H, d, J=12.0 Hz), 1.82-1.64 (2H, m), 1.49 (6H, dd, J=6.7, 1.1 Hz).

Example 2AB. ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone

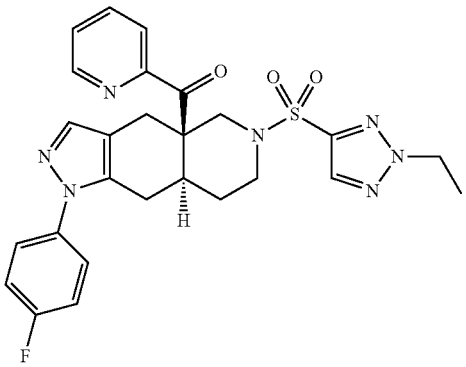 [SMILES: CCn1ncc(S(=O)(=O)N2CC[C@H]3Cc4c(cnn4-c4ccc(F)cc4)C[C@]3(C(=O)c3ccccn3)C2)n1]

LCMS: RT 2.43 min, m+H=536.2; 1H NMR (400 MHz, CDCl$_3$): 8.63 (1H, ddd, J=4.7, 1.6, 0.9 Hz), 7.84-7.77 (3H, m), 7.50-7.45 (2H, m), 7.43 (1H, ddd, J=7.0, 4.7, 1.6 Hz), 7.33 (1H, s), 7.17-7.11 (2H, m), 5.68 (1H, dd, J=12.4, 1.9 Hz), 4.51 (2H, q, J=7.3 Hz), 4.36 (1H, d, J=16.2 Hz), 3.99-3.92 (1H, m), 3.45 (1H, dd, J=16.2, 11.3 Hz), 2.69 (1H, dd, J=16.2, 6.0 Hz), 2.63-2.55 (2H, m), 2.52 (1H, d, J=12.3 Hz), 2.43 (1H, dq, J=13.4, 4.8 Hz), 1.80-1.71 (2H, m), 1.59 (3H, t, J=7.3 Hz).

Example 2AC. ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone

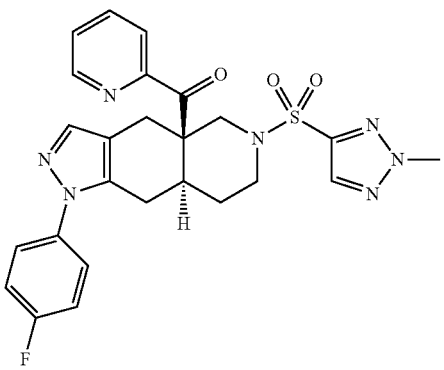 [SMILES: Cn1ncc(S(=O)(=O)N2CC[C@H]3Cc4c(cnn4-c4ccc(F)cc4)C[C@]3(C(=O)c3ccccn3)C2)n1]

LCMS: RT 2.31 min, m+H=522.2; 1H NMR (400 MHz, CDCl$_3$): δ 8.65 (1H, ddd, J=4.7, 1.6, 0.9 Hz), 7.84-7.77 (3H, m), 7.50-7.46 (2H, m), 7.43 (1H, ddd, J=7.1, 4.7, 1.6 Hz), 7.33 (1H, s), 7.17-7.11 (2H, m), 5.68 (1H, dd, J=12.4, 2.0 Hz), 4.36 (1H, d, J=16.2 Hz), 3.99-3.91 (1H, m), 4.25 (3H, s), 3.45 (1H, dd, J=16.2, 11.3 Hz), 2.70 (1H, dd, J=16.2, 6.0 Hz), 2.64-2.55 (2H, m), 2.53 (1H, d, J=12.4 Hz), 2.43 (1H, dq, J=13.4, 4.7 Hz), 1.80-1.71 (2H, m).

Example 2AD. ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone

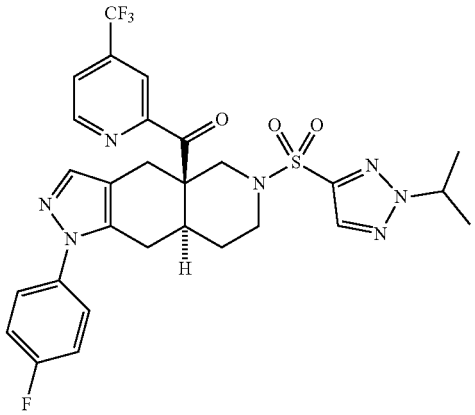 [SMILES: CC(C)n1ncc(S(=O)(=O)N2CC[C@H]3Cc4c(cnn4-c4ccc(F)cc4)C[C@]3(C(=O)c3cc(C(F)(F)F)ccn3)C2)n1]

LCMS: RT 2.79 min, m+H=618.3; 1H NMR (400 MHz, CDCl$_3$): δ 8.87 (1H, d, J=5.0 Hz), 8.10-8.09 (1H, m), 7.80 (1H, s), 7.66 (1H, dd, J=5.0, 1.0 Hz), 7.50-7.44 (2H, m), 7.32 (1H, s), 7.17-7.11 (2H, m), 5.64 (1H, dd, J=12.5, 2.0 Hz), 4.88 (1H, sept, J=6.6 Hz), 4.25 (1H, d, J=16.2 Hz), 3.99-3.91 (1H, m), 3.43 (1H, dd, J=16.2, 10.9 Hz), 2.71 (1H, dd, J=16.4, 6.0 Hz), 2.63-2.56 (2H, m), 2.54 (1H, d, J=12.4 Hz), 2.42 (1H, dq, J=13.4, 4.8 Hz), 1.86-1.75 (2H, m), 1.60 (6H, d, J=6.6 Hz).

Example 2AE. ((4aR,8aS)-6-((2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone

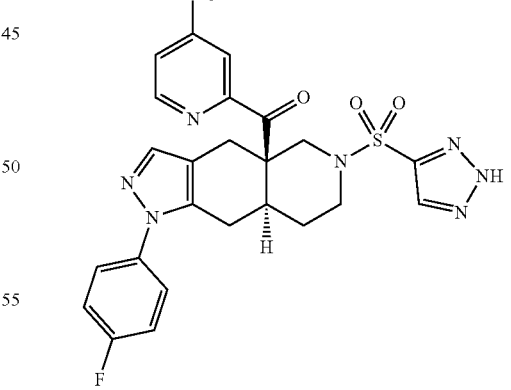

LCMS: RT 2.39 min, m+H=576.2; 1H NMR (400 MHz, CDCl$_3$): δ 8.87 (1H, d, J=5.0 Hz), 8.11-8.10 (1H, m), 7.93 (1H, s), 7.66 (1H, dd, J=5.0, 1.0 Hz), 7.50-7.45 (2H, m), 7.39 (1H, s), 7.19-7.13 (2H, m), 5.64 (1H, dd, J=12.5, 1.9 Hz), 4.27 (1H, d, J=16.2 Hz), 3.98-3.91 (1H, m), 3.42 (1H, dd, J=16.2, 11.3 Hz), 2.71 (1H, dd, J=16.6, 6.1 Hz), 2.66-2.59 (3H, m), 2.40 (1H, dq, J=13.5, 4.7 Hz), 1.85-1.74 (2H, m).

Example 2AF. ((4aR,8aS)-1-(4-fluorophenyl)-6-((1-isopropyl-1H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone

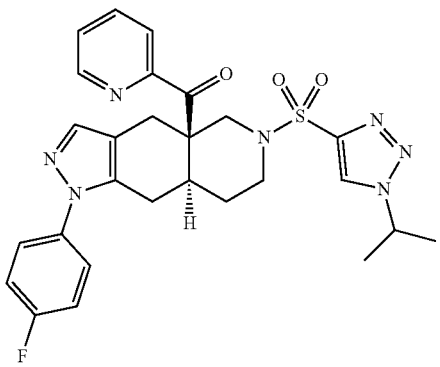 [SMILES: CC(C)n1cc(S(=O)(=O)N2CC[C@H]3Cc4c(cnn4-c4ccc(F)cc4)C[C@]3(C(=O)c3ccccn3)C2)nn1]

LCMS: RT 2.37 min, m+H=550.2; 1H NMR (400 MHz, CDCl$_3$): 8.65 (1H, ddd, J=4.7, 1.6, 0.9 Hz), 7.90 (1H, s), 7.84 (1H, ddd, J=8.0, 1.3, 0.9 Hz), 7.79 (1H, dt, J=7.3, 1.6 Hz), 7.51-7.46 (2H, m), 7.42 (1H, ddd, J=7.3, 4.7, 1.6 Hz), 7.34 (1H, s), 7.17-7.11 (2H, m), 5.70 (1H, dd, J=12.4, 2.0 Hz), 4.85 (1H, sept, J=6.7 Hz), 4.38 (1H, d, J=16.2 Hz), 4.01-3.92 (1H, m), 3.45 (1H, dd, J=16.4, 11.0 Hz), 2.81-2.68 (3H, m), 2.59 (1H, d, J=15.9 Hz), 2.43 (1H, dq, J=13.9, 5.0 Hz), 1.84-1.73 (2H, m), 1.59 (6H, dd, J=6.7, 2.0 Hz).

Example 2AG. ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-2-yl)methanone

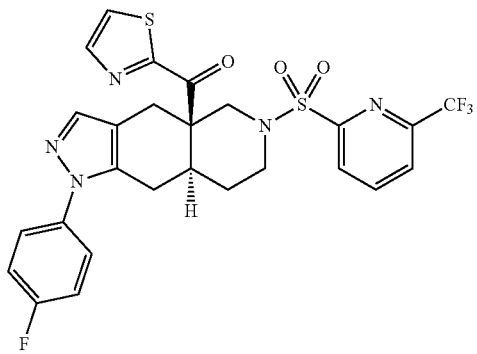 [SMILES: O=C(c1nccs1)[C@]12Cc3cnn(-c4ccc(F)cc4)c3C[C@@H]1CCN(S(=O)(=O)c1cccc(C(F)(F)F)n1)C2]

LCMS: RT 2.58 min, m+H=592.2; 1H NMR (400 MHz, CDCl$_3$): 1H NMR (400 MHz, CDCl$_3$) δ 8.07-8.01 (2H, m), 7.95 (1H, d, J=7.8 Hz), 7.83 (1H, d, J=7.8 Hz), 7.60 (1H, d, J=3.1 Hz), 7.48-7.45 (2H, m), 7.34 (1H, s), 7.16-7.12 (2H, m), 5.62 (1H, dd, J=12.9, 1.6 Hz), 4.24 (1H, d, J=16.1 Hz), 4.13-4.09 (1H, m), 3.42 (1H, dd, J=16.1, 11.6 Hz), 3.07-3.00 (2H, m), 2.72 (1H, dd, J=16.4, 6.1 Hz), 2.63 (1H, d, J=16.2 Hz), 2.50 (1H, dq, J=12.9, 5.0 Hz), 1.99-1.90 (1H, m), 1.81-1.78 (1H, m).

Example 2AH. ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-4-yl)methanone

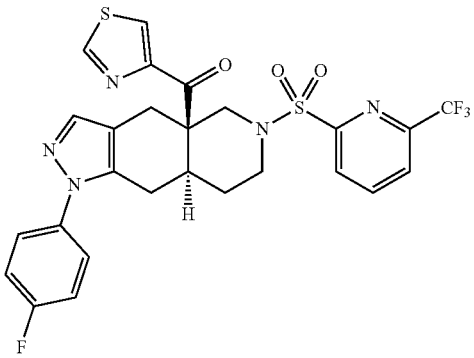 [SMILES: O=C(c1cscn1)[C@]12Cc3cnn(-c4ccc(F)cc4)c3C[C@@H]1CCN(S(=O)(=O)c1cccc(C(F)(F)F)n1)C2]

LCMS: RT 2.53 min, m+H=592.2; 1H NMR (400 MHz, CDCl$_3$): 1H NMR (400 MHz, CDCl$_3$) δ 8.83 (1H, d, J=2.1 Hz), 8.15 (1H, d, J=2.1 Hz), 8.07-8.03 (1H, m), 7.96 (1H, d, J=7.6 Hz), 7.82 (1H, dd, J=7.6, 0.9 Hz), 7.50-7.45 (2H, m), 7.33 (1H, s), 7.17-7.11 (2H, m), 5.58 (1H, dd, J=12.9, 2.0 Hz), 4.18 (1H, d, J=16.4 Hz), 4.10-4.06 (1H, m), 3.47 (1H, dd, J=16.2, 11.3 Hz), 3.04-2.97 (1H, m), 2.95 (1H, d, J=13.1 Hz), 2.70 (1H, dd, J=16.2, 6.1 Hz), 2.59-2.45 (2H, m), 1.95-1.97 (1H, m), 1.82-1.73 (1H, m).

Example 2AI. ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone

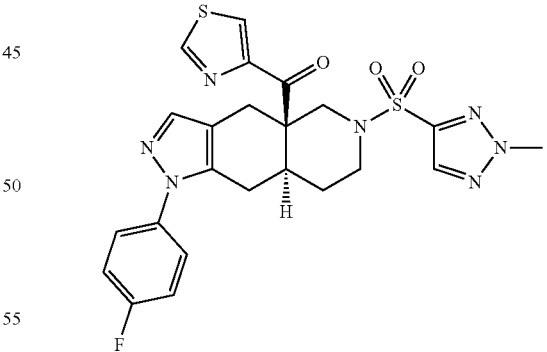

LCMS: RT 2.21 min, m+H=528.2; 1H NMR (400 MHz, CDCl$_3$): 1H NMR (400 MHz, CDCl$_3$) δ 8.85 (1H, d, J=2.0 Hz), 8.17 (1H, d, J=2.0 Hz), 7.82 (1H, s), 7.50-7.45 (2H, m), 7.34 (1H, s), 7.17-7.11 (2H, m), 5.53 (1H, dd, J=12.6, 2.1 Hz), 4.26 (3H, s), 4.19 (1H, d, J=16.4 Hz), 4.00-3.96 (1H, m), 3.46 (1H, dd, J=15.7, 10.9 Hz), 2.72-2.43 (5H, m), 1.84-1.73 (2H, m).

Example 2AJ. ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone

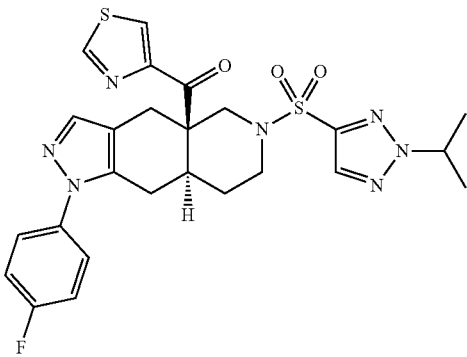 [SMILES: CC(C)n1ncc(S(=O)(=O)N2CC[C@H]3Cc4c(cnn4-c4ccc(F)cc4)C[C@]3(C(=O)c3cscn3)C2)n1]

LCMS: RT 2.46 min, m+H=556.2; 1H NMR (400 MHz, CDCl$_3$): 1H NMR (400 MHz, CDCl$_3$) δ 8.86 (1H, d, J=2.1 Hz), 8.17 (1H, d, J=2.1 Hz), 7.80 (1H, s), 7.50-7.45 (2H, m), 7.35 (1H, s), 7.17-7.11 (2H, m), 5.54 (1H, dd, J=12.6, 2.1 Hz), 4.89 (1H, sept, J=6.8 Hz), 4.19 (1H, d, J=16.4 Hz), 4.02-3.94 (1H, m), 3.46 (1H, dd, J=16.4, 12.0 Hz), 2.71-2.43 (5H, m), 1.84-1.72 (2H, m), 1.61 (6H, d, J=6.8 Hz).

Example 2AK. ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(thiazol-4-yl)methanone

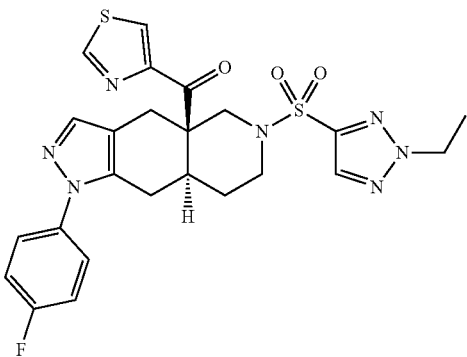 [SMILES: CCn1ncc(S(=O)(=O)N2CC[C@H]3Cc4c(cnn4-c4ccc(F)cc4)C[C@]3(C(=O)c3cscn3)C2)n1]

LCMS: RT 2.33 min, m+H=542.2; 1H NMR (400 MHz, CDCl$_3$): 1H NMR (400 MHz, CDCl$_3$) δ 8.87 (1H, d, J=2.0 Hz), 8.19 (1H, d, J=2.0 Hz), 7.83 (1H, s), 7.52-7.46 (2H, m), 7.36 (1H, s), 7.19-7.13 (2H, m), 5.55 (1H, dd, J=12.6, 2.2 Hz), 4.54 (2H, q, J=7.2 Hz), 4.20 (1H, d, J=16.4 Hz), 4.01-3.97 (1H, m), 3.48 (1H, dd, J=15.8, 11.0 Hz), 2.73-2.46 (5H, m), 1.87-1.77 (2H, m), 1.62 (3H, t, J=7.2 Hz).

Example 3. Human Glucocorticoid Receptor (GR) Fluorescence Polarisation (FP) Binding Assay The following is a description of a FP assay for measuring compound inhibition of labelled glucocorticoid binding to the human recombinant GR.

The binding affinity of test compounds was determined using a FP binding assay using human recombinant GR (PanVera P2812) and a fluorescent labelled glucocorticoid ligand (Fluorome GS Red) (PanVera P2894). The presence of inhibitors prevents the formation of a GS Red/GR complex resulting in a decrease in the measured polarisation value. The change in polarisation value in the presence of test compounds is used to calculate the binding affinity of the compound for GR.

This assay was performed in 384 well, black, round-bottom, polypropylene micro titre plates in a final volume of 20 μl. The assay contained 5 μl 1 nM GR (final concentration), 5 μl 0.5 nM Fluorome GS Red (final concentration) in the presence of 10p test compounds. Positive control wells (high polarisation) receive, 10 μl 2% (v:v) DMSO vehicle (1% (v/v) final concentration)+5 μl 1 nM GR and 5 μl 0.5 nM Fluorome GS Red. Negative control wells (low polarisation) receive 10 μl 2 μM dexamethasone (1 μM final concentration)+5 μl 1 nM GR and 5 μl 0.5 nM Fluorome GS Red. Assay blank background wells (used for normalisation) receive 15 μl 1×GS screening buffer+5 μl GR.

For the IC$_{50}$ determination (concentration of compound that displaces 50% of the bound GS Red), compounds were tested at eight different concentrations in duplicate in two independently performed experiments. Compounds were prepared as solubilised solids at 10 mM in DMSO. On the day of assay, an 8 point half-log serial dilution (55 μl DMSO+25 μl compound solution) was prepared. A 1:50 dilution (1 μl compound solution+49 μl 1×GR screening buffer) was prepared for each compound. The compounds were prepared at 2× final assay concentration.

The reagents were added to the 384 well micro titre plates in the following order: 10 μl test compound/vehicle/1 μM dexamethasone, 5 μl Fluorome GS Red and 5 μl GR. The plates were mixed and incubated for 4 hour at room temperature. FP was measured using an Envision Excite plate reader with 535 nm excitation and 590 nm emission interference filters.

Milli-polarisation (mP) values were calculated using the below equation:

$$mP=1000*(S-G*P)/(S+G*P)$$

where S and P are assay blank background subtracted fluorescence units, G=G-factor (1.07).

Compound IC$_{50}$ values were calculated by plotting a [compound] v. % inhibition curve and fitting the data to a 4-parameter logistic fit equation. Compound K$_i$ (equilibrium dissociation constant) values were determined from the experimental IC$_{50}$ values using a ligand depletion correction equation (see below) assuming the antagonists were competitive inhibitors with respect to dexamethasone (Pharmacologic Analysis of Drug Receptor Interactions, 2$^{nd}$ Ed., p 385-410, 1993, Raven Press, New York).

$$K_i = \frac{(L_b)*(IC_{50})*(K_d)}{(L_o)*(R_o)+L_b*(R_o-L_o+L_b-K_d)}$$

| | |
|---|---|
| Equilibrium dissociation constant of GS red ligand (K$_d$) | 0.3 nM |
| Bound tracer concentration (L$_b$) | 0.3 nM |
| Total tracer concentration (L$_o$) | 0.5 nM |
| Total receptor concentration (R$_o$) | 1.0 nM |

Reagents:
10× GR screening buffer (100 mM potassium phosphate pH 7.4, 200 mM Na$_2$MoO$_4$, 1 mM EDTA, 20% (v/v)

DMSO). To prepare 1× GR screening buffer, combine 1 ml 10×GR screening buffer (PanVera P2814)+1 ml stabilising peptide (PanVera P2815)+7.95 ml 4° C. MQ water. Add 50 µL 1M DTT, vortex and place on ice until use.

Example 4. HepG2 Tyrosine Aminotransferase (TAT) Assay

Glucocorticoid mediated activation of TAT occurs by transactivation of glucocorticoid response elements in the TAT promoter by glucocorticoid receptor-agonist complex. The following protocol describes an assay for measuring induction of TAT by dexamethasone in HepG2 cells (a human liver hepatocellular carcinoma cell line; ECACC, UK).

TAT activity was measured as outlined in the literature by A. Ali et al., J. Med. Chem., 2004, 47, 2441-2452. Dexamethasone induced TAT production with an average $EC_{50}$ value (half-maximal effect) of 20 nM.

HepG2 cells were cultured using MEME media supplemented with 10% (v/v) foetal bovine serum; 2 mM L-glutamine and 1% (v/v) NEAA at 37° C., 5%/95% (v/v) $CO_2$/air. The HepG2 cells were counted and adjusted to yield a density of $0.125 \times 10^6$ cells/ml in RPMI 1640 without phenol red, 10% (v/v) charcoal stripped FBS, 2 mM L-glutamine and seeded at 25,000 cells/well in 200 µl into 96 well, sterile, tissue culture micro titre plates, and incubated at 37° C., 5% $CO_2$ for 24 hours Growth media was removed and replaced with assay media {RPMI 1640 without phenol red, 2 mM L-glutamine+ 10 µM forskolin}. Test compounds were screened against a challenge of 100 nM dexamethasone. Compounds were serially half log diluted in 100% (v/v) dimethylsulphoxide from a 10 mM stock. Then an 8-point half-log dilution curve was generated followed by a 1:100 dilution into assay media to give a 0× final assay [compound]: this resulted in final assay [compound] that ranged 10 to 0.003 µM in 0.1% (v/v) dimethylsulfoxide.

Test compounds were pre-incubated with cells in microtitre plates for 30 minutes at 37° C., 5/95 (v/v) $CO_2$/air, before the addition of 100 nM dexamethasone and then subsequently for 20 hours to allow optimal TAT induction.

HepG2 cells were then lysed with 30 µL of cell lysis buffer containing a protease inhibitor cocktail for 15 minutes at 4° C. 155 µL of substrate mixture was then added containing 5.4 mM Tyrosine sodium salt, 10.8 mM alpha ketoglutarate and 0.06 mM pyridoxal 5' phosphate in 0.1M potassium phosphate buffer (pH 7.4). After 2 hours incubation at 37° C. the reaction was terminated by the addition of 15 µL of 10M aqueous potassium hydroxide solution, and the plates incubated for a further 30 minutes at 37° C. The TAT activity product was measured by absorbance at λ 340 nm.

$IC_{50}$ values were calculated by plotting % inhibition (normalised to 100 nM dexamethasone TAT stimulation) v. [compound] and fitting the data to a 4 parameter logistic equation. $IC_{50}$ values were converted to Ki (equilibrium dissociation constant) using the Cheng and Prusoff equation, assuming the antagonists were competitive inhibitors with respect to dexamethasone.

TABLE 1

Activity Data

| Example | $R^1$ | $R^{1a}$ | Ring J | $R^2$ | GR binding (nM) | TAT (nM) |
|---|---|---|---|---|---|---|
| 1A | pyridin-2-yl | H | phenyl | 4-$CF_3$ | ++ | ++ |
| 1B | pyridin-2-yl | H | phenyl | 3,4-Cl | + | ++ |
| 1C | pyridin-2-yl | H | phenyl | 3,4-F | + | ++ |
| 2A | pyridin-2-yl | H | 1,2,3-triazol-4-yl | 2-nPr | +++ | +++ |
| 2B | pyridin-2-yl | H | pyrazol-4-yl | 1-nPr | +++ | +++ |
| 2C | pyridin-2-yl | 4-$CF_3$ | 1,2,3-triazol-4-yl | 2-Me | ++ | +++ |
| 2D | pyridin-2-yl | 4-$CF_3$ | pyrazol-4-yl | 1-nPr | +++ | +++ |
| 2E | thiazol-2-yl | H | pyrazol-4-yl | 1-nPr | +++ | +++ |
| 2F | pyridin-2-yl | H | phenyl | 3-F | + | ++ |
| 2G | pyridin-2-yl | H | phenyl | 3-$CF_3$ | + | ++ |
| 2H | pyridin-2-yl | 4-$CF_3$ | pyrazol-4-yl | 1-Me | + | ++ |
| 2I | pyridin-2-yl | 4-$CF_3$ | pyrazol-3-yl | 1-Me | ++ | ++ |
| 2J | pyridin-2-yl | 4-$CF_3$ | pyrazol-5-yl | 1-Me | + | ++ |
| 2K | pyridin-2-yl | 4-$CF_3$ | pyrazol-4-yl | 1-Et | ++ | ++ |
| 2L | pyridin-2-yl | 4-$CF_3$ | pyrazol-5-yl | 2-Et | + | ++ |
| 2M | thiazol-2-yl | H | phenyl | 4-$CF_3$ | + | ++ |
| 2N | pyridin-2-yl | H | 1,2,3-triazol-4-yl | 2-iPr | +++ | +++ |
| 2O | pyridin-2-yl | 4-$CF_3$ | 1,2,3-triazol-4-yl | 2-Et | ++ | +++ |
| 2P | pyridin-2-yl | 4-$CF_3$ | 1,2,3-triazol-4-yl | 1-Me | + | ++ |
| 2Q | pyridin-2-yl | H | pyridin-2-yl | 6-$CF_3$ | ++ | +++ |
| 2R | pyridin-2-yl | 4-Me | 1,2,3-triazol-4-yl | 2-Me | +++ | +++ |
| 2S | thiazol-4-yl | H | 1,2,3-triazol-4-yl | 2-nPr | +++ | ++ |
| 2T | pyridin-2-yl | H | phenyl | 3-CN | + | ++ |
| 2U | pyridin-2-yl | H | phenyl | 3-F, 4-$CF_3$ | + | ++ |
| 2V | pyridin-2-yl | H | 4-methyl-3,4-dihydro-2H-pyrido[3,2-b][1,4]oxazin-7-yl | | + | ++ |
| 2W | thiazol-2-yl | H | 1,2,3-triazol-5-yl | 1-nPr | + | + |
| 2X | pyridin-2-yl | 4-$CF_3$ | 1,2,3-triazol-5-yl | 1-Me | + | + |
| 2Y | thiazol-2-yl | H | 1,2,3-triazol-4-yl | 2-Me | + | + |
| 2Z | thiazol-2-yl | H | 1,2,3-triazol-4-yl | 2-iPr | +++ | ++ |
| 2AA | pyridin-2-yl | H | pyrazol-4-yl | 1-iPr | +++ | ++ |
| 2AB | pyridin-2-yl | H | 1,2,3-triazol-4-yl | 2-Et | +++ | ++ |
| 2AC | pyridin-2-yl | H | 1,2,3-triazol-4-yl | 2-Me | + | ++ |
| 2AD | pyridin-2-yl | 4-$CF_3$ | 1,2,3-triazol-4-yl | 2-iPr | +++ | +++ |
| 2AE | pyridin-2-yl | 4-$CF_3$ | 1,2,3-triazol-4-yl | H | + | + |
| 2AF | pyridin-2-yl | H | 1,2,3-triazol-4-yl | 1-iPr | + | ++ |
| 2AG | thiazol-2-yl | H | pyridin-2-yl | 6-$CF_3$ | ++ | ++ |
| 2AH | thiazol-4-yl | H | pyridin-2-yl | 6-$CF_3$ | ++ | +++ |
| 2AI | thiazol-4-yl | H | 1,2,3-triazol-4-yl | 2-Me | + | ++ |
| 2AJ | thiazol-4-yl | H | 1,2,3-triazol-4-yl | 2-iPr | +++ | +++ |
| 2AK | thiazol-4-yl | H | 1,2,3-triazol-4-yl | 2-Et | | +++ |

In Table 1, GR Binding compounds with a $K_i$ value of less than 0.5 nM are designated with +++; compounds with a $K_i$ value from 0.5 nM to less than 1.0 nM are designated with ++; and compounds with a $K_i$ value of at least 1.0 nM are designated with +. TAT activity with a $K_i$ value of less than 20 nM are designated with +++, compounds with a $K_i$ value from 20 nM to less than 100 nM are designated with ++; and compounds with a $K_i$ value of at least 100 nM are designated with +.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating cachexia comprising administering to a subject in need thereof a therapeutically effective amount of a compound having the formula:

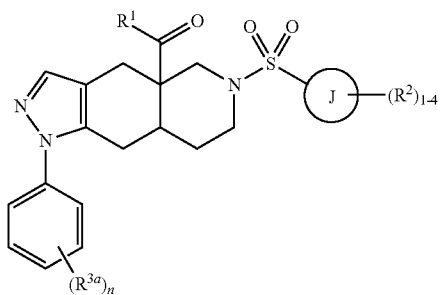

(I)

wherein
$R^1$ is selected from the group consisting of pyridine and thiazole, optionally substituted with 1-4 groups each independently selected from $R^{1a}$;
each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;
ring J is selected from the group consisting of phenyl, pyridine, pyrazole, and triazole;
each $R^2$ is independently selected from the group consisting of hydrogen, $C_{1-6}$ alkyl, halogen, $C_{1-6}$ haloalkyl, and —CN;
$R^{3a}$ is F;
subscript n is an integer from 0 to 3;
or salts thereof,
wherein said subject is in need of treatment for cachexia,
thereby treating cachexia.

2. The method of claim 1, wherein $R^1$ is selected from the group consisting of 2-thiazole, 4-thiazole, 5-thiazole, 2-pyridine, 3-pyridine, and 4-pyridine.

3. The method of claim 1, wherein $R^1$ is selected from the group consisting of 2-thiazole, 4-thiazole and 2-pyridine.

4. The method of claim 1, wherein $R^1$ is pyridine.

5. The method of claim 1, wherein $R^1$ is thiazole.

6. The method of claim 1, wherein $R^{1a}$ is independently selected from the group consisting of hydrogen, $C_{1-6}$ alkyl, and $C_{1-6}$ haloalkyl.

7. The method of claim 1, wherein $R^{1a}$ is independently selected from the group consisting of hydrogen, methyl, and trifluoromethyl.

8. The method of claim 1, wherein ring J is selected from the group consisting of phenyl, 2-pyridine, 3-pyridine, 4-pyridine, 1-pyrazole, 3-pyrazole, 4-pyrazole, 5-pyrazole, 1,2,3-triazol-4-yl, 1,2,3,-triazol-5-yl, 1,2,4-triazol-3-yl, and 1,2,4-triazol-5-yl.

9. The method of claim 1, wherein $R^2$ is independently selected from the group consisting of hydrogen, methyl, ethyl, n-propyl, isopropyl, F, Cl, —$CF_3$ and —CN.

10. The method of claim 1, the compound having the structure:

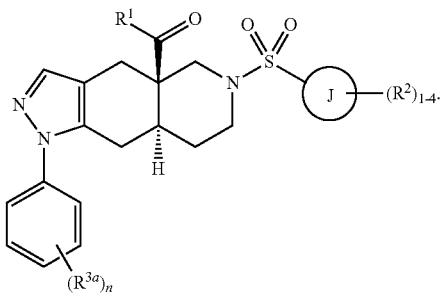

11. The method of claim 1, wherein the compound is selected from the group consisting of:
((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone,
((4aR,8aS)-6-((3,4-dichlorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone,
((4aR,8aS)-6-((3,4-difluorophenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone,
((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone,
((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone,
((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
((4aR,8aS)-1-(4-fluorophenyl)-6-((1-propyl-1H-pyrazol-4-yl)sulfonyl)-4,4a,5,6,7,8,8a,9-octahydro-1H-pyrazolo[3,4-g]isoquinolin-4a-yl)(thiazol-2-yl)methanone,
((4aR,8aS)-1-(4-fluorophenyl)-6-((3-fluorophenyl)sulfonyl)-4,4a,5,6,7,8,8a,9-octahydro-1H-pyrazolo[3,4-g]isoquinolin-4a-yl)(pyridin-2-yl)methanone,
((4aR,8aS)-1-(4-fluorophenyl)-6-((3-(trifluoromethyl)phenyl)sulfonyl)-4,4a,5,6,7,8,8a,9-octahydro-1H-pyrazolo[3,4-g]isoquinolin-4a-yl)(pyridin-2-yl)methanone,
((4aR,8aS)-1-(4-fluorophenyl)-6-((1-methyl-1H-pyrazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
((4aR,8aS)-1-(4-fluorophenyl)-6-((1-methyl-1H-pyrazol-3-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone,
((4aR,8aS)-1-(4-fluorophenyl)-6-((1-methyl-1H-pyrazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-6-((1-ethyl-1H-pyrazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-6-((1-ethyl-1H-pyrazol-5-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((4-(trifluoromethyl)phenyl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((1-methyl-1H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(4-methylpyridin-2-yl)methanone, ((4aR,8aS)-1-(4-fluorophenyl)-6-((2-propyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone, 3-(((4aR,8aS)-1-(4-fluorophenyl)-4a-picolinoyl-4a,5,7,8,8a,9-hexahydro-1H-pyrazolo[3,4-g]isoquinolin-6(4H)-yl)sulfonyl)benzonitrile, ((4aR,8aS)-6-((3-fluoro-4-(trifluoromethyl)phenyl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((4-methyl-3,4-dihydro-2H-pyrido[3,2-b][1,4]oxazin-7-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((1-propyl-1H-1,2,3-triazol-5-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((1-methyl-1H-1,2,3-triazol-5-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((1-isopropyl-1H-pyrazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-6-((2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(4-(trifluoromethyl)pyridin-2-yl)methanone, ((4aR,8aS)-1-(4-fluorophenyl)-6-((1-isopropyl-1H-1,2,3-triazol-4-yl)sulfonyl)-4,4a,5,6,7,8,8a,9-octahydro-1H-pyrazolo[3,4-g]isoquinolin-4a-yl)(pyridin-2-yl)methanone, ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-2-yl)methanone, ((4aR,8aS)-1-(4-fluorophenyl)-6-((6-(trifluoromethyl)pyridin-2-yl)sulfonyl)-4,4a,5,6,7,8,8a,9-octahydro-1H-pyrazolo[3,4-g]isoquinolin-4a-yl)(thiazol-4-yl)methanone, ((4aR,8aS)-1-(4-fluorophenyl)-6-((2-methyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone, ((4aR,8aS)-1-(4-fluorophenyl)-6-((2-isopropyl-2H-1,2,3-triazol-4-yl)sulfonyl)-4,4a,5,6,7,8,8a,9-octahydro-1H-pyrazolo[3,4-g]isoquinolin-4a-yl)(thiazol-4-yl)methanone, and ((4aR,8aS)-6-((2-ethyl-2H-1,2,3-triazol-4-yl)sulfonyl)-1-(4-fluorophenyl)-4,4a,5,6,7,8,8a,9-octahydro-1H-pyrazolo[3,4-g]isoquinolin-4a-yl)(thiazol-4-yl)methanone.

12. The method of claim 1, wherein the compound has the structure:

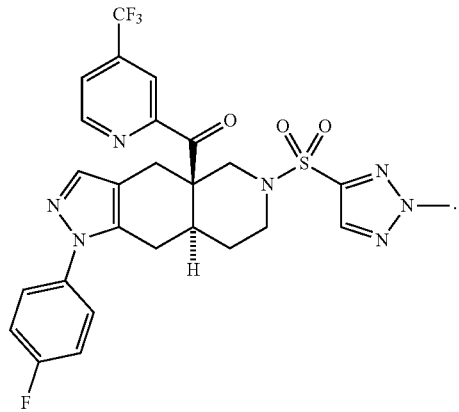 [SMILES: Cn1ncc(S(=O)(=O)N2CC[C@H]3Cc4c(cnn4-c4ccc(F)cc4)C[C@]3(C(=O)c3cc(C(F)(F)F)ccn3)C2)n1]

13. The method of treating cachexia of claim 1, wherein said method comprises treating said cachexia through modulating a glucocorticoid receptor, comprising administering to a subject in need thereof, a therapeutically effective amount of a compound having the formula (I), thereby modulating a glucocorticoid receptor effective to treat cachexia.

14. The method of claim 13, wherein the compound has the structure:

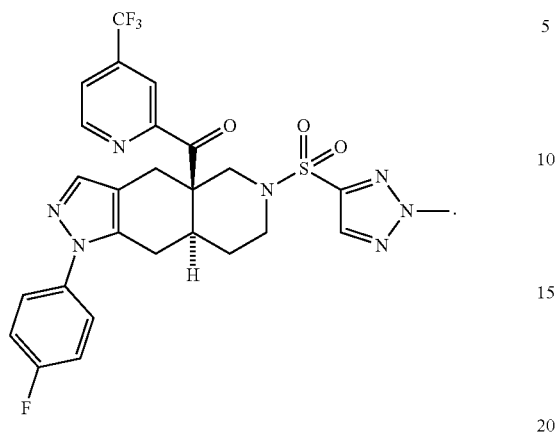

15. The method of treating cachexia of claim 11, wherein said method comprises treating said cachexia through modulating a glucocorticoid receptor, comprising administering to a subject in need thereof, a therapeutically effective amount of a compound recited in claim 11, thereby modulating a glucocorticoid receptor effective to treat cachexia.

* * * * *